(12) United States Patent
Homer

(10) Patent No.: US 11,259,962 B1
(45) Date of Patent: Mar. 1, 2022

(54) SYSTEMS AND METHODS FOR PATIENT ALIGNMENT AND TREATMENT

(71) Applicant: STROMA MEDICAL CORPORATION, Irvine, CA (US)

(72) Inventor: Gregg Homer, Irvine, CA (US)

(73) Assignee: Stroma Medical Corporation, Irvine, CA (US)

(*) Notice: Subject to any disclaimer, the term of this patent is extended or adjusted under 35 U.S.C. 154(b) by 0 days.

(21) Appl. No.: 17/238,083

(22) Filed: Apr. 22, 2021

Related U.S. Application Data

(60) Provisional application No. 63/165,686, filed on Mar. 24, 2021.

(51) Int. Cl.
   *A61F 9/08* (2006.01)
   *A61F 9/008* (2006.01)
   (Continued)

(52) U.S. Cl.
   CPC .............. *A61F 9/008* (2013.01); *A61B 34/25* (2016.02); *A61G 15/02* (2013.01); *A61G 15/125* (2013.01);
   (Continued)

(58) Field of Classification Search
   CPC .............. A61F 9/008; A61F 2009/0035; A61F 2009/00842; A61F 2009/00844;
   (Continued)

(56) References Cited

U.S. PATENT DOCUMENTS 3,984,146 A * 10/1976 Krestel .................. A61G 15/02
                                                              297/330
6,306,127 B2 * 10/2001 Homer .................... A61F 9/008
                                                              128/898
(Continued)

FOREIGN PATENT DOCUMENTS

WO    2001003569    8/2001
WO    2002062259    8/2002

OTHER PUBLICATIONS

"Iris pigmentation and pigmented lesions: an ultrastructural study," Trans Am Ophthalmol Soc. 1988;86:581-687. PMID: 2979031; PMCID: PMC1298824.
(Continued)

*Primary Examiner* — Ahmed M Farah
(74) *Attorney, Agent, or Firm* — Perkins Coie LLP

(57) ABSTRACT

A system for supporting and aligning a patient during a color alteration procedure includes a laser system that delivers a laser in a first direction. A control computer may be adjacent the laser system for controlling the laser system. The control computer system may include a user interface in a first plane substantially perpendicular to the first direction. The system may include a patient support structure having a patient support surface extending in a second direction substantially perpendicular to the first direction and configured to be adjustable to set a patient position or alignment relative to the laser system. Coarse adjustment hardware may be configured to cause automated and/or manual adjustments to the patient support surface in the first direction. Fine adjustment hardware may be configured to cause automated fine adjustments to the patient support surface in the first direction based on instructions received from the control computer.

27 Claims, 14 Drawing Sheets

(51) Int. Cl.
*A61G 15/02* (2006.01)
*A61B 34/00* (2016.01)
*A61G 15/12* (2006.01)
*A61F 9/00* (2006.01)

(52) U.S. Cl.
CPC . *A61B 2034/258* (2016.02); *A61F 2009/0035* (2013.01); *A61F 2009/00846* (2013.01); *A61F 2009/00876* (2013.01); *A61F 2009/00878* (2013.01); *A61F 2009/00897* (2013.01)

(58) Field of Classification Search
CPC .. A61F 2009/00846; A61F 2009/00876; A61F 2009/00878; A61F 2009/00897; A61B 34/25; A61B 2034/252; A61B 2034/254; A61B 2034/258; A61G 15/02; A61G 15/10; A61G 15/12; A61G 15/125
USPC .................................. 606/4, 10–12; 128/898
See application file for complete search history.

(56) References Cited

U.S. PATENT DOCUMENTS

| | | | | |
|---|---|---|---|---|
| 8,206,379 | B2* | 6/2012 | Homer | A61F 9/00817 606/4 |
| 9,155,658 | B2* | 10/2015 | Heitel | A61F 9/008 |
| 9,421,131 | B2* | 8/2016 | Watanabe | A61F 9/00827 |
| 10,744,034 | B2 | 8/2020 | Homer | |
| 11,160,685 | B1* | 11/2021 | Homer | A61F 9/00802 |
| 2014/0343541 | A1* | 11/2014 | Scott | A61F 2/16 606/4 |
| 2018/0085257 | A1* | 3/2018 | Horvath | A61F 9/00834 |
| 2019/0099226 | A1* | 4/2019 | Hallen | H04N 13/324 |
| 2020/0054489 | A1* | 2/2020 | Thyzel | A61F 9/00802 |

OTHER PUBLICATIONS

"Image-Based Modeling of the Human Eye" IEEE Transactions On Visualization And Computer Graphics, vol. 15, No. 5, Sep./Oct. 2009.
"Don't it make my blue eyes brown: heterochromia and other abnormalities of the iris" Eye (2012) 26, 29-50; Published online Oct. 7, 2011; Presented at the Oxford Ophthalmological Congress 2010.
"Scheimpflug Camera-Based Stereo-Digital Image Correlation for Full-Field 3D Deformation Measurement," Hindawi Journal of Sensors, vol. 2019, Article ID 5391827, 11 pages (Oct. 10, 2019), https://doi.org/10.1155/2019/539182.
"Introduction To OCT" http://obel.ee.uwa.edu.au/research/fundamentals/introduction-oct/ Date unknown, downloaded Nov. 9, 2020.
"American National Standard for Safe Use of Lasers," ANSI Z136.1-2007, ISBN-13: 978-0-912035.65-9 & ISBN-10: 0-912035-65-X, (May 2007).
"Development of Close Proximity Wireless Technology with Integrated On-Chip Antenna," https://www.renesas.com/us/en/about/press-room/development-close-proximity-wireless-technology-integrated-chip-antenna, Jun. 29, 2010.

* cited by examiner

SYSTEMS AND METHODS FOR PATIENT ALIGNMENT AND TREATMENT

RELATED APPLICATION(S)

This application claims priority to and the benefit of U.S. Provisional Application No. 63/165,686, filed Mar. 24, 2021, titled "Systems And Methods For Patient Alignment And Treatment," which is hereby incorporated by reference.

FIELD OF THE INVENTION

The invention relates to patient support systems suitable for medical procedures related to changing an eye color of a patient.

BACKGROUND

The use of lasers for eye surgery has increased recently. However, while laser eye surgery is a known option for the correction of one or more vision problems such as nearsightedness (myopia), farsightedness (hyperopia), and astigmatism, little interest has been shown to operations other than those for correcting vision problems. For example, advancements in laser eye surgeries have focused on operations through which a laser may reshape a patient's cornea and have ignored other parts of a patient's eye and procedures therefor.

SUMMARY

In view of this, methods and systems are discussed herein for delivering laser light to an iris of a patient. In particular, the methods and systems discussed herein are for performing an eye color changing procedure through this delivery of laser light. For example, changing a person's eye color may be performed by delivering laser light to portions of the eye that are responsible for giving the eye its color (e.g., the iris).

To achieve this effect, the methods and systems must overcome several technical hurdles. For example, in conventional medical procedures involving the eye (e.g., LASIK), it does not matter how the patient's head is supported. Accordingly, it is natural for such procedures to have the patient in an upright position whereby their head is supported by their neck muscles. However, when the neck muscles are engaged, it is the body's natural response to continuously have small movements of the head (e.g., between 150-350 microns) along the optical axis of the eye. There may also be similar corresponding small changes in the orientation of the eye and that the persons head may rotate along one or more axes in the process of supporting the head via the neck muscles. Such movements may be detrimental to the disclosed eye color alteration procedure. Thus, conventional head stabilization devices, while they may provide some assistance, still suffer from the problem that the patient's neck muscles are engaged.

In view of these technical hurdles, the systems and methods discussed herein provide a patient support structure that allows neck muscles of the patient to be disengaged during the color alteration procedure. Also discussed herein are related systems to facilitate the treatment, including, for example, having detached physician and technician consoles and methods for confirming the patient's identity prior to the procedure via iris or retinal scans.

The systems and methods overcome the shortcomings of conventional systems by providing a patient support structure for setting a patient position or alignment for performing the color alteration procedure. This may include, for example, an adjustable head support element that may cause the patient's head to be supported without engagement of their neck muscles. The patient support structure may be configured to allow coarse and/or fine adjustments of the patient's head and/or eye. A rangefinder may be included to determine precise distances between the laser system and the iris, for proper patient positioning. Related to this, there may be dedicated and detached physician and technician consoles that may control aspects of the procedure and/or display patient data. Image sensors may also be utilized to generate scans of the patient's iris or retina for patient identification, which along with patient medical record data, may be displayed at the consoles described above.

In one aspect, a system for supporting and aligning a patient during a color alteration procedure may include a laser system for performing the color alteration procedure. The laser system may deliver a laser in a first direction. A control computer system may be adjacent to the laser system for controlling the laser system during the color alteration procedure and may include a user interface in a first plane substantially perpendicular to the first direction. The system may also include a patient support structure having a patient support surface extending in a second direction substantially perpendicular to the first direction and configured to be adjustable to set a patient position or alignment relative to the laser system. The patient support structure may also have coarse adjustment hardware configured to cause automated and/or manual adjustments to the patient support structure in the first direction. Similarly, the patient support structure may include fine adjustment hardware configured to cause automated fine adjustments to the patient support surface in the first direction based on instructions received from the control computer.

In another interrelated aspect, there may be a tangible, non-transitory, machine-readable medium storing instructions that, when executed by a data processing apparatus, causes the data processing apparatus to perform operations comprising those of any of the above method embodiments.

In yet another interrelated aspect, a system may include one or more processors and memory storing instructions that, when executed by the processors, cause the processors to effectuate operations comprising those of any of the above method embodiments.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification, "a portion" refers to a part of, or the entirety of (i.e., the entire portion), a given item (e.g., data) unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

The present disclosure provides improved methods and systems for facilitating medical procedures to change the eye color of a patient. Such medical procedures may involve locating and aligning a patient (e.g., including the eye of the patient) in a proper manner that allows accurate delivery of laser light to portions of the eye such that a biological reaction occurs that alters the pigment structure of the eye and thereby changes its color. Determining and maintaining the proper position and alignment to use based on the needs of the procedure, safety to the patient, and variations from patient to patient may be critical to a successful outcome. Also, to facilitate interaction with the patient and efficient treatment delivery, the present disclosure contains embodiments of separate and dedicated console(s) that may be utilized by a physician and/or a technician.

Figure 1:
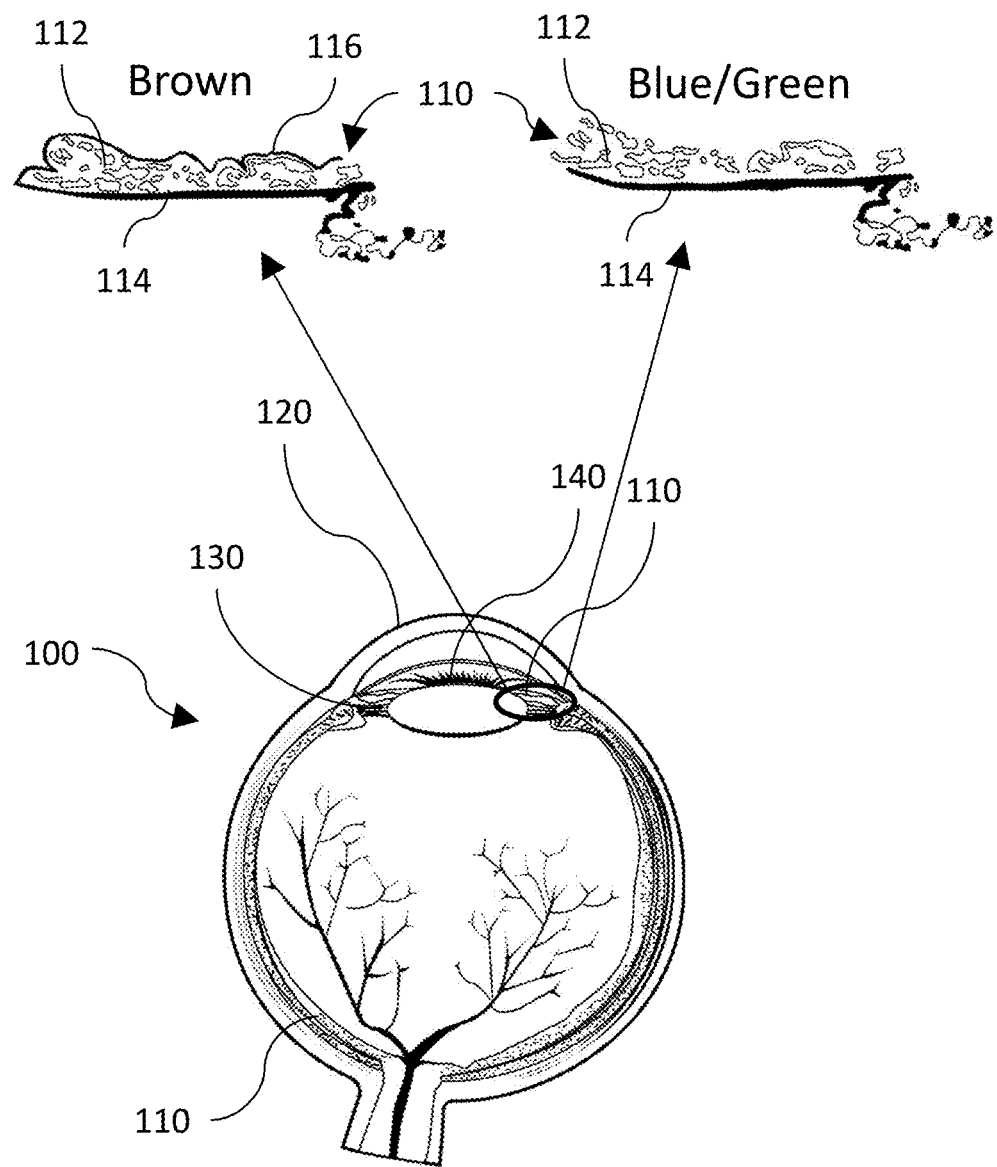
FIG. 1 shows a simplified diagram of the eye and iris.

Before describing the color alteration procedure, which is applicable to many embodiments of the present disclosure, a brief overview of the anatomy of the eye is provided. As shown in FIG. 1, eye 100 is composed of several anatomical structures, a few of which are discussed below. Central to the present disclosure, the iris 110 is responsible for the color of the eye. Other portions of the eye include, for example, cornea 120, lens 130, pupil 140, and retina 150. While care should be taken to avoid damaging any part of the eye, in the practice of laser safety, special precautions should be taken to avoid directing unwanted laser light through the pupil and into the lens as this part of the eye naturally focuses light onto the retina. Such focusing of already intense laser light may result in injury to the retinal nerves.

Shown in the insets above the eye are two examples of irises. The example on the left is a depiction of an iris 110 in a person with brown eyes. The example on the right depicts an iris 110 of a person with blue or green eyes. The perceived color is due to light reaching the eye being separated into its component wavelengths by stromal fibers in the middle region of the iris—referred to as the iris stroma 112. The separation is similar to the separation exhibited when light passes through a prism. In both cases, the iris has a posterior surface 114 that contains a fairly thick (several cells deep) layer of pigmentation that primarily absorbs visible light wavelengths longer than blue or green. However, in the example on the left for a person with brown eyes, there is an additional anterior surface that contains brown pigment, herein referred to as "stromal pigment" 116. The brown stromal pigment gives the eye a brown color. Eyes without the stromal pigment reflect mostly blue or green light as described above, giving the eye a blue or green color.

A brief summary of a color alteration procedure as referenced herein is provided. Laser light may be delivered to the stromal pigment to cause an increase in temperature of the stromal pigment. This process may be repeated several times to repeatedly raise and lower the temperature of the stromal pigment. This raising and lowering of the temperature causes the body to deploy macrophages (part of the body's natural immune response) to the stromal layer. These macrophages then remove a portion of the stromal pigment responsible for giving the eye its brown color. Repeated procedures may be performed to provide varying degrees of color change to make the eye appear a deeper blue/green. The delivery of the laser light may be in a scanning pattern (e.g., a spiral pattern surrounding the pupil or a raster pattern avoiding the pupil) to deliver the treatment to the entire iris.

Figure 2:
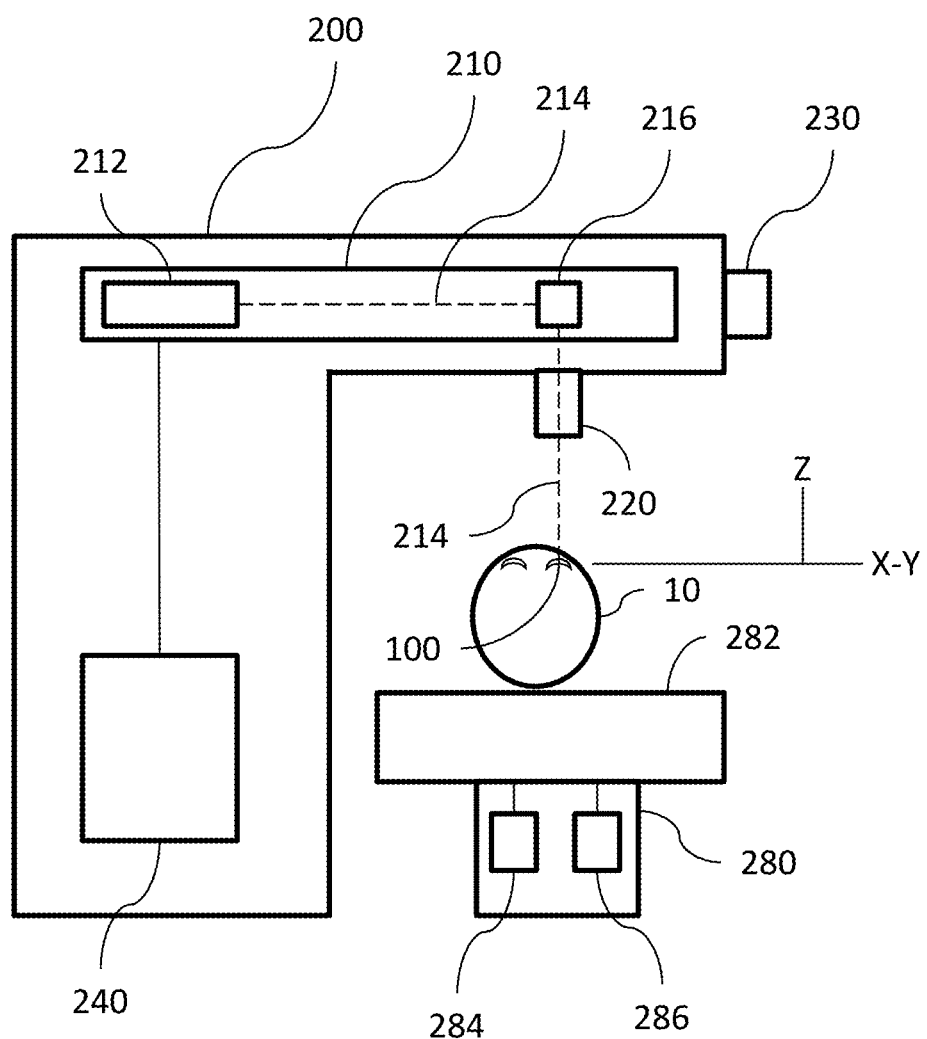
FIG. 2 shows a simplified diagram of a laser system and patient positioning system in accordance with one or more embodiments.

FIG. 2 shows a simplified diagram of a laser system and patient positioning system in accordance with one or more embodiments. One embodiment of the overall system 200 may include the laser system 210 and a patient positioning system 280. The head of patient 10 (with eyes 100) is shown supported by the patient positioning system in a location suitable for the color alteration procedure. The laser system may include the laser head 212 which provides laser light 214. The laser head may include components to generate laser light at varying wavelengths, for example, at 1064 nm or 532 nm (Nd:YLF or Nd:YAG). Exemplary pulse widths may be in the 5-300 ns with repetition rates of 5-300 kHz and an $M^2<1.2$.

The laser head may include an energy source (aka a pump or pump source), a gain medium, and two or more mirrors that form an optical resonator. Exemplary energy sources include: electrical discharges; flashlamps; arc lamps; output from another laser; and chemical reactions. Exemplary gain media include: liquids (e.g., dyes comprising chemical solvents and chemical dyes); gases (e.g., carbon dioxide, argon, krypton, and helium-neon); solids (e.g., crystals and glasses, such as yttrium-aluminum garnet, yttrium lithium fluoride, sapphire, titanium-sapphire, lithium strontium aluminum fluoride, yttrium lithium fluoride, neodymium glass, and erbium glass), which may be doped with an impurity (e.g., chromium, neodymium, erbium, or titanium ions) and may be pumped by flashlamps or output from another laser; and semiconductors, with uniform or differing dopant distribution (e.g., laser diode).

Embodiments of the laser head may include an optical frequency multiplier (e.g., a frequency doubler and sum-frequency generator), where the laser output frequency is increased by passing it through a non-linear crystal or other material. The benefit of an optical frequency multiplier is that it increases the range of frequencies/wavelengths available from a given gain medium. The non-linear material may be inserted into the optical resonator for one-step frequency multiplication, or the fundamental (i.e. non-multiplied) output beam may be passed through the non-linear material after leaving the optical resonator for two-step frequency multiplication. Exemplary non-linear materials for frequency doubling may include: lithium niobate, lithium tantalate, potassium titanyl phosphate, or lithium triborate. Two-step frequency tripling is typically performed by frequency doubling a fraction of the fundamental output beam in a first step. The doubled fraction of the fundamental beam and the non-doubled remainder of the fundamental beam are then coupled into a second non-linear frequency tripling material in a second step for sum-frequency mixing. Exemplary non-linear materials for frequency tripling may include potassium dihydrogen phosphate.

One combination of gain medium and optical frequency multiplier is Nd:YAG with a frequency doubler. The natural harmonic of a laser beam generated by an Nd:YAG gain medium is a wavelength of 1,064 nm, which is then halved to 532 nm by the frequency doubler. This wavelength may be utilized as: (a) it falls within the visible light spectrum (i.e., green), thereby passing through the clear cornea with little or no absorption; (b) it has a high absorption coefficient in stromal pigment, thereby effecting selective photothermolysis in the anterior stromal pigment of the iris; and (c) the wavelength is relatively short, thereby limiting the depth of penetration and avoiding unwanted damage to the IPE. Any other combination of gain media and optical frequency multiplication that meets these three criteria is also may also be implemented in some embodiments.

Laser pulse widths may be in the nanosecond range (i.e., from below 1 nanosecond to 1 microsecond) and the pulse repetition rate may be in the kilohertz range (i.e., from below 1 kHz to 1 MHz). Some embodiments may have a pulse width between 5 ns and 300 ns, which may provide improved pigment denaturation. Q-switching may be utilized as a preferred pulsing method as it tends to be optimally suited to the nanosecond pulse width. Some embodiments include active Q-switching with a modulator device.

As used herein, "laser" means any device capable of generating a beam of optical radiation, whether in the infrared, visible light, or ultraviolet light spectrum. The term "laser" is not intended to restrict: (a) the properties of the optical radiation in terms of monochromaticity or coherence (e.g., divergence or directionality); (b) whether the radiation is continuous or pulsed; (c) if pulsed, the specific pulse width (e.g., zeptosecond attosecond, femtosecond, picosecond, nanosecond, millisecond, or microsecond); (d) the repetition rate; (e) the laser power; (f) the wavelength or frequency of the beam; (g) the number of wavelengths or frequencies, i.e., single v. multi-frequency output (e.g., intense pulsed light); (h) the number of beams, i.e., single v. multiple beams (e.g., splitting of a single beam or generating multiple beams from multiple lasers); or (i) the gain medium.

As used herein, "laser power" may mean either $W/cm^2$ or $J/cm^2$, depending on the context—as they are related by the exposure time. The MPE may be expressed in either of those units. For example, MPE may include the maximum level of laser radiation to which a fundus may be exposed without hazardous effects or biological changes in the eye.

Accordingly, when the specification refers to a laser power in terms of an MPE, the exact value of the laser power depends on, among other things, the beam spot size, pulse duration, or wavelength, and whether the laser is pulsed or continuous, etc. Thus, the determination of the MPE provides a basis for the skilled person to determine the laser power in the various embodiments disclosed herein.

As used herein, when referring to "reducing," "lowering," "less," etc., in the context of adjusting the laser power, this is understood to mean that the laser system may reduce the laser power from a current value to a lower (nonzero) value while still delivering laser light in some respect. These definitions also include redirecting the laser beam (e.g., to a beam dump) such that the delivered laser power is reduced. These definitions also include turning off the laser system (i.e., lowering the laser power to zero). Lastly, reducing the laser power may also include performing any of the above in a repetitive fashion thereby lowering the duty cycle of the laser beam or performing any combination of the above in an intermittent fashion.

Galvos systems 216 (also referred to as the x-y beam guidance system) may be included in the laser system and may include adjustable mirrors to provide a means of delivering the laser light to various locations on an X-Y plane (typically the plane of the iris where the laser light usually focused). Further implementations of the laser system may include, for example rangefinders and/or optical tracking systems, which may include cameras to determine an X-Y deviation of the center of the eye relative to the optical axis of the laser system.

In some embodiments, the x-y beam guidance system may scan the beam spot about the iris surface. The scanning parameters may include the size, shape, and position of the target region, the line and spot separation between each beam spot, and the predetermined scan pattern. The computer imaging software may determine the size, shape, and position of the target region based upon iris images captured by the x-y imaging system and transmitted to the computer for processing. Once processed, the size, shape, and position data may be transmitted to the scanning program to drive the x-y beam guidance system. New iris images may be captured at predetermined intervals and transmitted to the computer for processing throughout the procedure. Captured images are compared, and if they indicate a change in iris position, the computer imaging software calculates the x-y deltas and transmits the shift coordinates to the scanning program, which in turn executes the shift in the scanning position. In some procedures, a topical cholinergic agonist such as pilocarpine hydrochloride ophthalmic solution 2% (e.g., Isopto Carpine 2% from Alcon, Geneva, Switzerland) may be instilled in the target eye prior to treatment to constrict the pupil, flatten out the iris surface, and mitigate changes in the iris size and shape during the procedure. The line and spot separation between each beam spot may be predetermined and programmed into the scanning program prior to treatment. In some cases, the spot and line separation place each beam spot tangent to the others throughout the target region. The scan pattern may be raster (including slow-x/fast-y and slow-y/fast-x), spiral (including limbus to pupil and pupil to limbus), vector, and Lissajous scans.

In one embodiment, the x-y beam guidance system may scan the beam spot about the iris surface by means of controlled deflection of the laser beam. Embodiments utilizing beam steering in two dimensions may drive the beam spot about the two-dimensional surface of the iris. Beam motion may be periodic (e.g., as in barcode scanners and resonant galvanometer scanners) or freely addressable (e.g., as in servo-controlled galvanometer scanners). Exemplary beam steering in two dimensions may include: rotating one mirror along two axes (e.g., one mirror scans in one dimension along one row and then shifts to scan in one dimension along an adjacent); and reflecting the laser beam onto two closely spaced mirrors mounted on orthogonal axes.

There are numerous methods for controlled beam deflection, both mechanical and non-mechanical. Exemplary non-mechanical methods may include: steerable electro-evanescent optical refractor or SEEOR; electro-optical beam modulation; and acousto-optic beam deflection. Exemplary mechanical methods may include: nanopositioning using a piezo-translation stage; the micro-electromechanical system or MEMS controllable microlens array; and controlled deflection devices. Mechanically controlled deflection devices may include: motion controllers (e.g., motors, galvanometers, piezoelectric actuators, and magnetostrictive actuators); optical elements (e.g., mirrors, lenses, and prisms), affixed to motion controllers; and driver boards (aka servos) or similar devices to manage the motion controllers. The optical elements may have a variety of sizes, thicknesses, surface qualities, shapes, and optical coatings, the selection of which depends upon the beam diameter, wavelength, power, target region size and shape, and speed requirements. Some embodiments may utilize optical elements that are flat or polygonal mirrors. An embodiment of the motion controller may include a galvanometer, including a rotor and stator (to manage torque efficiency) and a position detector (PD) (to manage system performance). An exemplary PD may include one or more illumination diodes, masks, and photodetectors. Driver boards may be analog or digital. Scan motion control might also comprise one or more rotary encoders and control electronics that provide the suitable electric current to the motion controller to achieve a desired angle or phase. The installed scanning program disclosed above may be configured to collect measured scan and target region data.

The x-y beam guidance system may apply the laser spot to all or any portion of the anterior iris surface. Treated fractions of the anterior iris surface may include the following (which are inclusive and do not take into account any spared tissue due to line and/or spot separations): greater than ¼; greater than 30%; greater than ¼; greater than ½; and greater than ¾.

The system can include one or types of rangefinding apparatuses to measure the Z distance from a reference point to the target (e.g., the iris surface). As used herein, the Z direction is taken to be the vertical direction, perpendicular to the X-Y plane (e.g., the iris surface). A component referred to herein as optical exit 220 may be provided to allow the exiting of laser light to reach the eye. Optical exit 220 may include windows, lenses (e.g., dichroic lenses), mirrors, shutters, or other optical components. In some implementations, the system may include platform control 230, which may be configured to provide coarse adjustment (manually or automatic computer-controlled) in the X, Y, or Z directions. The platform control 230 may also be configured to perform fine adjustments similar to the above, with such fine adjustments implemented by computer control. Also included in some implementations are control computer and power supplies, depicted by element 240 in FIG. 1. Alternatively, control computers or electronics and some or all of the needed power supplies need not be contained in the system 200 as depicted in FIG. 1, but may be distributed in other locations or networked to be operatively connected to the laser system. Examples of rangefinding apparatuses may include systems that perform triangulation, time-of-flight measurements, etc., with one specific example being an optical coherence tomography system. Further discussion of rangefinding and/or tracking apparatuses is provide throughout the application.

The laser system may deliver a laser in a first direction, which in the example of FIG. 2 is the Z axis. The control computer system 240 may be adjacent to the laser system and configured to control the laser system during the color alteration procedure. By "adjacent," this means in a housing of the laser system, in a larger housing that contains the laser system and generally encloses the overall device itself, such as shown in FIG. 2. In some embodiments, "adjacent" may be in the treatment room or nearby treatment room and connected wired or wirelessly to the laser system. In some embodiments, the control computer system may include a user interface in a first plane substantially perpendicular to the first direction. For example, there may be a display such as a computer screen that provides information on the laser system, the patient, or the treatment.

Patient support structure 280 may have a patient support surface 282 extending in a second direction that may be substantially perpendicular to the first direction (e.g., in the example of FIG. 2, being in the X-Y plane). The patient support structure may be configured to be adjustable to set a patient position or alignment relative to the laser system. As used herein, the term "patient position" or "position" means the location of the patient's head or eye (e.g., an X, Y, Z coordinate). As used herein, the term "patient alignment" or "alignment" means the orientation of the patient's head or eye, and may include tilt, roll, or other sort of angular measure that describes the orientation of the eye. As used herein, the term "substantially perpendicular" means that the patient support surface provides support for the patient such that (optionally in combination with other components such as the head support element, described below) the neck muscles may be disengaged. This does not mean that any particular component or fraction of components of the patient support surface need be strictly perpendicular to the first direction. For example, a patient support surface may include a couch-type structure that may be oriented horizontally or in a reclining position (thus substantially perpendicular to the first direction). Similarly, in other embodiments described later herein, the patient support surface may be an adjustable seat (forming part of the patient support structure), where the seat is generally horizontal for the patient to sit on.

In some embodiments, the laser system may be immovable such that only the patient support surface is configured to position (or orient) the patient. As shown in FIG. 2, the laser system may be cantilevered over the patient support surface with the laser beam coming downward towards the patient who is located on the patient support surface. However, in other embodiments, such as that shown in FIG. 6, it is contemplated that laser system may be below the patient in the sense that laser may be delivered from below rather than above.

In some embodiments, Z actuator 286 may include (or be part of) coarse adjustment hardware configured to cause automated and/or manual adjustments to the patient support surface in the first direction. Examples of coarse adjustment hardware may include, for example, stepper motors, gear assemblies, band assemblies, etc. Some embodiments may have similar coarse adjustment hardware integrated with X-Y actuator 284 for coarse adjustments in the X-Y plane (i.e., allowing movement of the patient support surface substantially perpendicular to the first direction). While in some embodiments, such coarse adjustment hardware may be manual (e.g., movable via rollers, tracks, hand cranks, etc.), in some embodiments a computer may automate and control the coarse adjustment hardware. In some embodiments, the system may generate a projection of a crosshair or similar reticle to locate where the patient's head and/or eye should be. The positioning technician (or alternatively the system utilizing machine vision to scan and locate the projected crosshair on the patient) may then position the patient appropriately before performing optional fine adjustments.

In some embodiments, Z actuator 286 may include (or be part of) fine adjustment hardware configured to cause automated and/or manual adjustments to the patient support surface in the first direction. Examples of fine adjustment hardware may include hydraulic actuators, pneumatic actuators, piezoelectric actuators, etc. Some embodiments may have similar fine adjustment hardware integrated with X-Y actuator 284 for fine adjustments in the X-Y plane. While most embodiments of fine adjustment hardware may be computer controlled, it is contemplated that some embodiments may be manually adjustable (e.g., via high-ratio gear assemblies, etc.).

As used herein, the terms "coarse" and "fine" have their plain meaning in that "coarse" adjustments are of a lower resolution (i.e., larger step size) than "fine" adjustments. However, examples of coarse resolutions may include 0.5 cm, 1 cm, 2 cm, 5 cm, or 10 cm. Examples of "fine" resolutions may include 0.1 mm, 0.5 mm, 1 mm, 2 mm, or 5 mm. Such values are approximate in that it is understood that physical systems contain varying degrees of lash or hysteresis that may affect the particulars of a given resolution. In some embodiments, due to the precise nature of the disclosed color alteration procedure, fine adjustments made utilizing the fine adjustment hardware may be performed automatically by the system based on a treatment plan for altering an eye color of the patient. In some embodiments, similar adjustments may be made utilizing the coarse adjustment hardware. For example, the coarse adjustment hardware may be controlled by the computer to put the patient in approximately the correct location. Then, the fine adjustment hardware may be controlled to exactly position the patient for treatment. As the treatment progresses, the two types of hardware and their respective actuators may work in concert to position the patient as needed.

Figure 3:
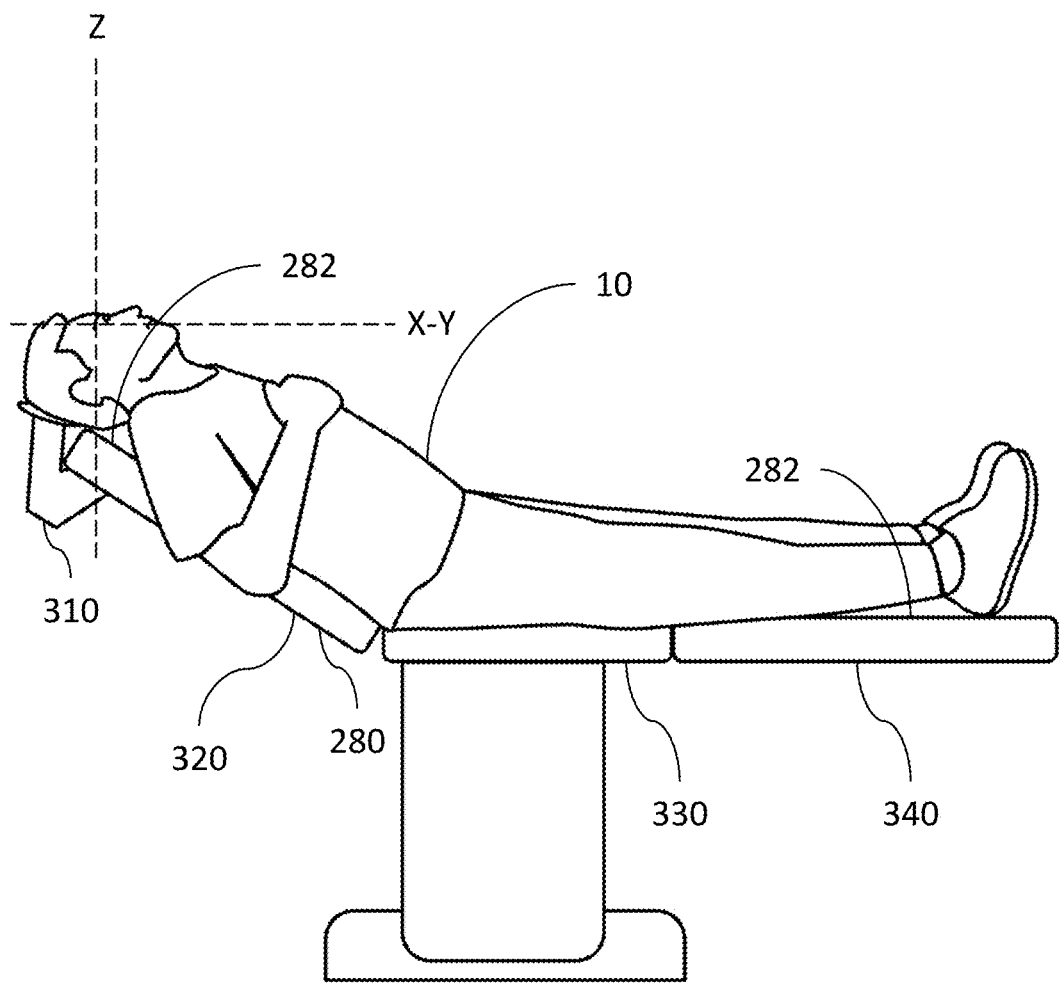
FIG. 3 shows a simplified patient support structure having an upper reclining portion in accordance with one or more embodiments.

FIG. 3 shows a simplified patient support structure having an upper reclining portion in accordance with one or more embodiments. As depicted in FIG. 3, the patient support structure may include a head support element 310 mounted to the upper reclining portion 320 and configured to cause a head of the patient 10 to be supported without engagement of neck muscles. Examples of head support elements may include, for example, headrests, cradles, padded prongs, etc. The head support element may support the head in one or more locations (e.g., supporting the head at multiple specific points, rather than a single-piece headrest). In some embodiments, the head support element may be independently adjustable in any combination of X, Y, Z as well as any combination of rotation (right or left), tilt (forward or back), etc. Such adjustable embodiments of the head support element may further include an adjustment mechanism similar to the coarse adjustment hardware and/or fine adjustment hardware described above. The head support element may be set with a similar resolution to that described above for coarse and/or fine adjustments. As used herein, "without engagement," "disengaged," or similar expressions as relating to neck muscles mean that the muscles are relaxed and providing little, if any, support to the head such that unwanted involuntary patient movement of the head and/or eye is reduced or eliminated. As disclosed, this is embodied by systems that allow the person to lean forward or back such that the patient support structure is providing support rather than the neck muscles.

As also shown in FIG. 3, the patient support structure may include a lower support portion 330 in addition to an upper reclining portion. The angle between the upper reclining portion and the lower support portion may be manually or automatically controlled by the physician and/or the control system. In some cases, a balance may be reached between patient comfort and/or physical needs (e.g., for patients unable to be fully in the supine position) and disengagement of the neck muscles for the treatment procedure. There may also be an adjustable leg portion 340 connected to the lower support portion 310 to provide for adjusting a patient's legs. This adjustable leg portion 340 is discussed further with reference to FIG. 5.

Figure 4:
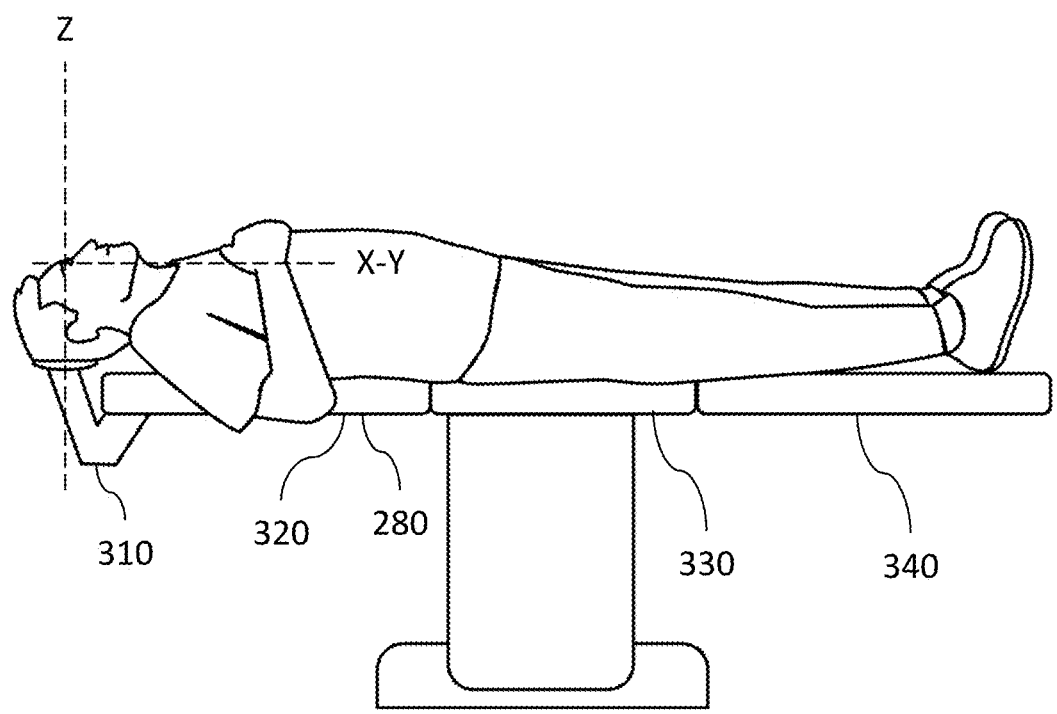
FIG. 4 shows a view of the simplified patient support structure of FIG. 3 with the upper reclining portion fully horizontal in accordance with one or more embodiments.

FIG. 4 shows a view of the simplified patient support structure of FIG. 3 with the upper reclining 320 portion fully horizontal in accordance with one or more embodiments. As described above, exemplary embodiments of the patient support structure may include ones where the patient is able to fully recline (i.e., the entire patient support surface 282 forms a substantially horizontal plane). Also shown in this embodiment is the head support element suitably adjusted such that the patient is in the proper location and alignment for the procedure.

Figure 5:
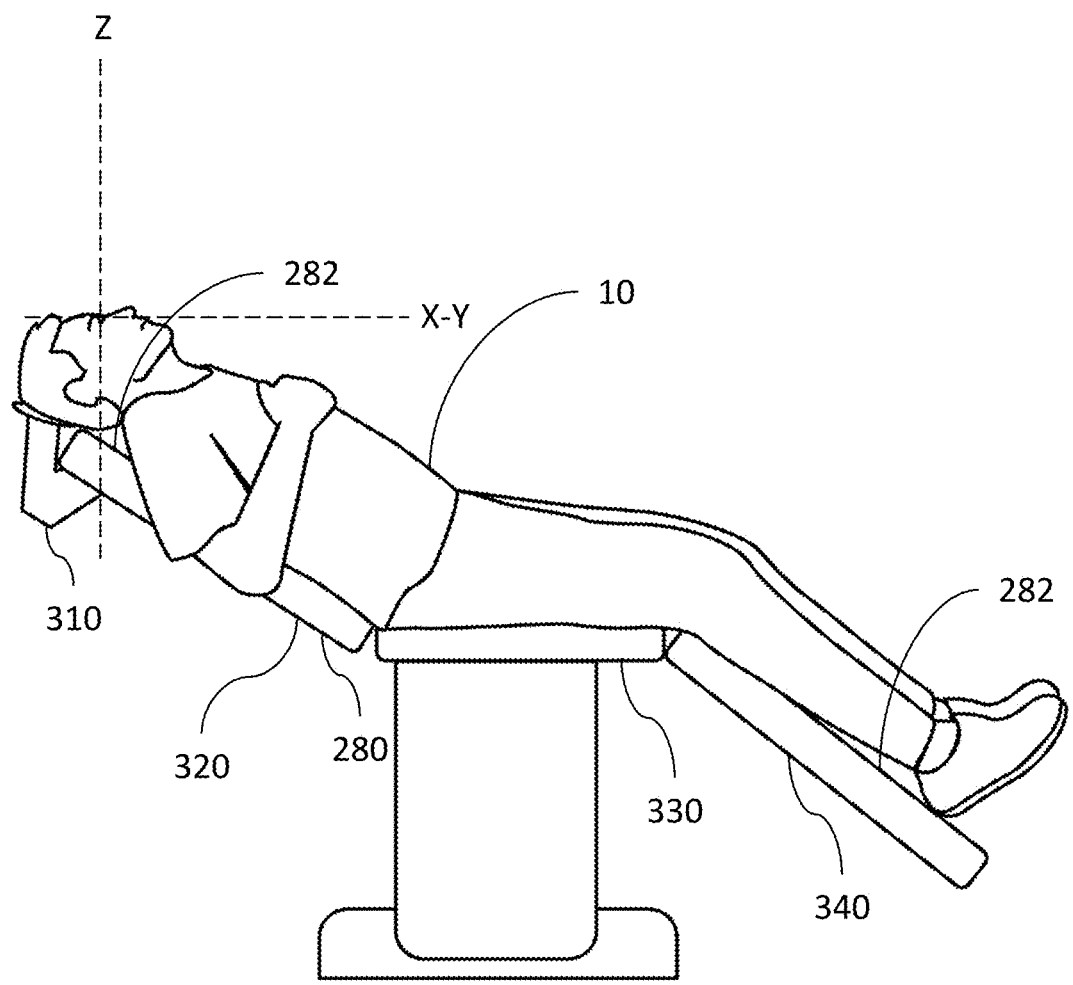
FIG. 5 shows a view of the simplified patient support structure of FIG. 3 having an adjustable leg portion in accordance with one or more embodiments.

FIG. 5 shows a view of the simplified patient support structure of FIG. 3 having an adjustable leg portion 340 in accordance with one or more embodiments. As shown, the adjustable leg portion may be mounted to the lower support portion. The adjustable leg portion may be adjustable in either a coarse or fine adjustment manner as described above. Again, it is important in many embodiments for the patient to have disengaged neck muscles. Due to the interconnectedness of a person's musculoskeletal structure, even improper positioning of the legs may cause engagement of muscles throughout the body, including the neck muscles. As such, in some embodiments, a large number of degrees of freedom may be utilized in the patient support structure to provide the needed positioning of the patient, not just at the head, but in other locations throughout the body, for proper disengagement of the neck muscles.

Figure 6:
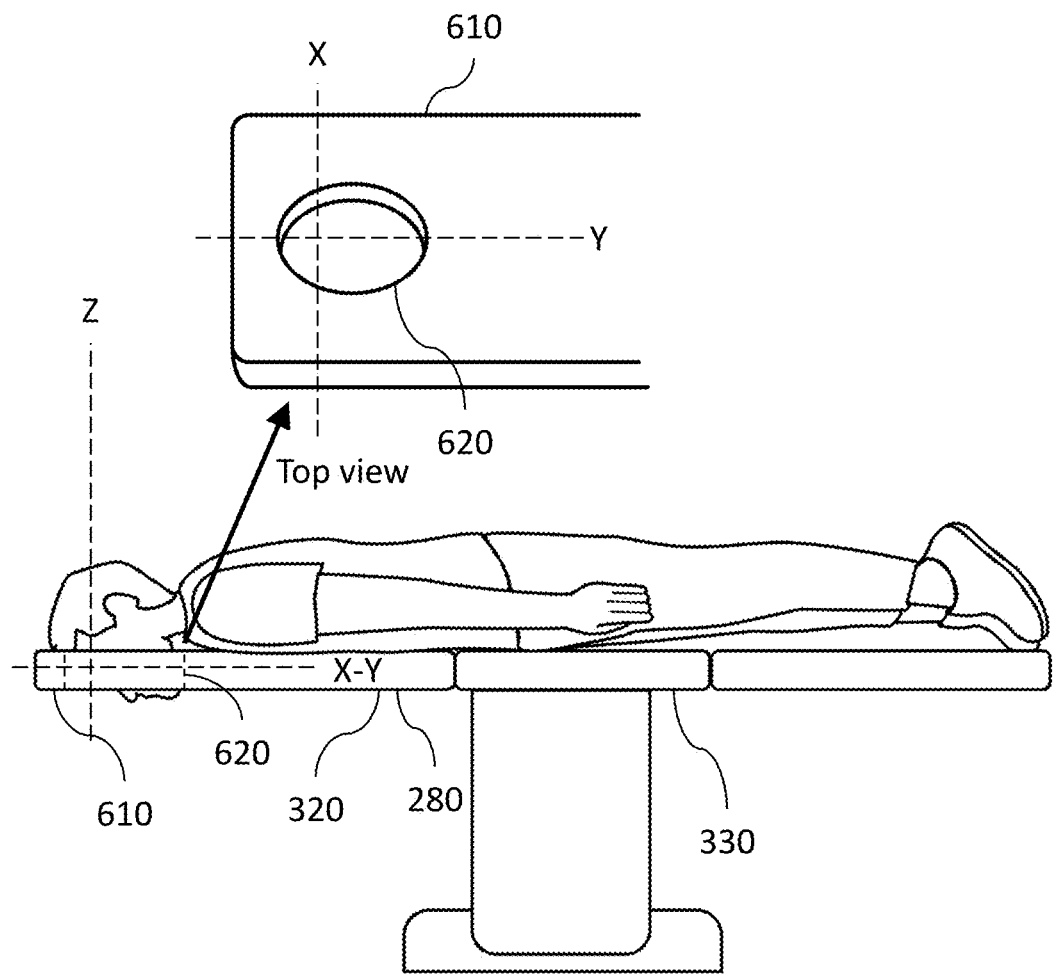
FIG. 6 shows a simplified patient support structure with a head support element having an aperture in accordance with one or more embodiments.

FIG. 6 shows a simplified patient support structure 280 with a head support element 610 having an aperture 620 in accordance with one or more embodiments. In some embodiments, the head support element may include an aperture in the patient support surface. The aperture is also depicted in the upper inset showing a partial top view of the patient support structure. As shown in FIG. 5, the head support element may be configured to support the head with the patient in a face-down position on the patient support surface. To allow access to the patient for the procedure, the aperture may allow access to the eye by the patient's face being at least partially within (or through) the aperture. Such embodiments may be combined with other features described in the present disclosure, for example, patient support surfaces that have the capability of reclining.

In some embodiments, patient support structures may be multifunctional in that for some patients, a head support element 310 of the sort depicted in FIGS. 3-5 may be attached to the patient support structure as described above. However, the same patient support structure may have a second head support element 610 in the form of an aperture 620 at a location in the upper reclining portion 320 such that when in the position shown in FIG. 6, the aperture 6120 may be utilized rather than the (possibly detachable) headrest-type head support element 310. Such embodiments have the advantage of allowing the patient support structure to interface with both types of laser systems—where the laser is directed from above or below the patient.

Figure 7:
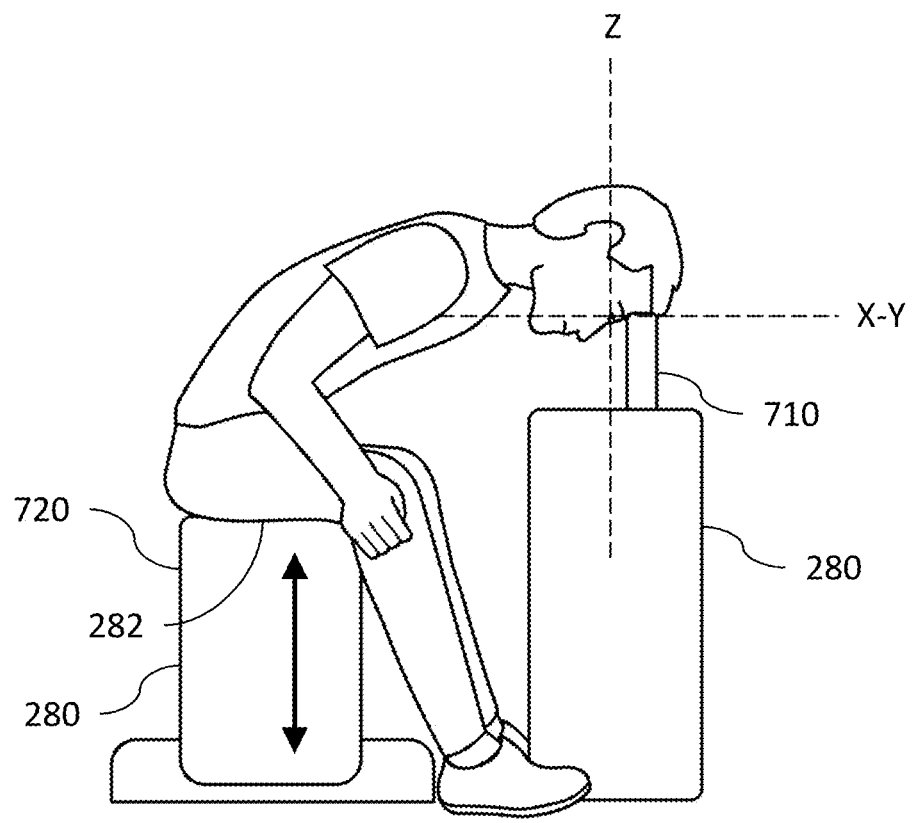
FIG. 7 shows a simplified patient support structure as part of an adjustable seat in accordance with one or more embodiments.

FIG. 7 shows a simplified patient support surface 282 as part of an adjustable seat 720 in accordance with one or more embodiments. As previously mentioned, laser systems may provide laser beams from below the patient. As shown in FIG. 7, the patient support structure 280 may include a head support element 710 and an adjustable seat 720. In the example shown, the patient is leaning forward with their head resting on the head support element 710 with the eye exposed to the laser beam (in embodiments where the laser system directs the beam from below). To adjust the position and alignment of the patient, the adjustable seat 720 (with patient support surface 282) may be configured to move in the first direction as indicated by the double-arrow. Such motion relative to the head support element may change the tilt of the eye when the head is resting on the head support element. For example, with the adjustable seat at a higher Z position, the patient would naturally be in a more horizontal, face-down position, which would have the effect of rotating the patient's eye about an axis in the X-Y plane. It is also contemplated that the head support element and the adjustable seat may each also have actuators similar to those described above (e.g., in X, Y, and/or Z and at a fine and/or coarse resolution).

Figure 8:
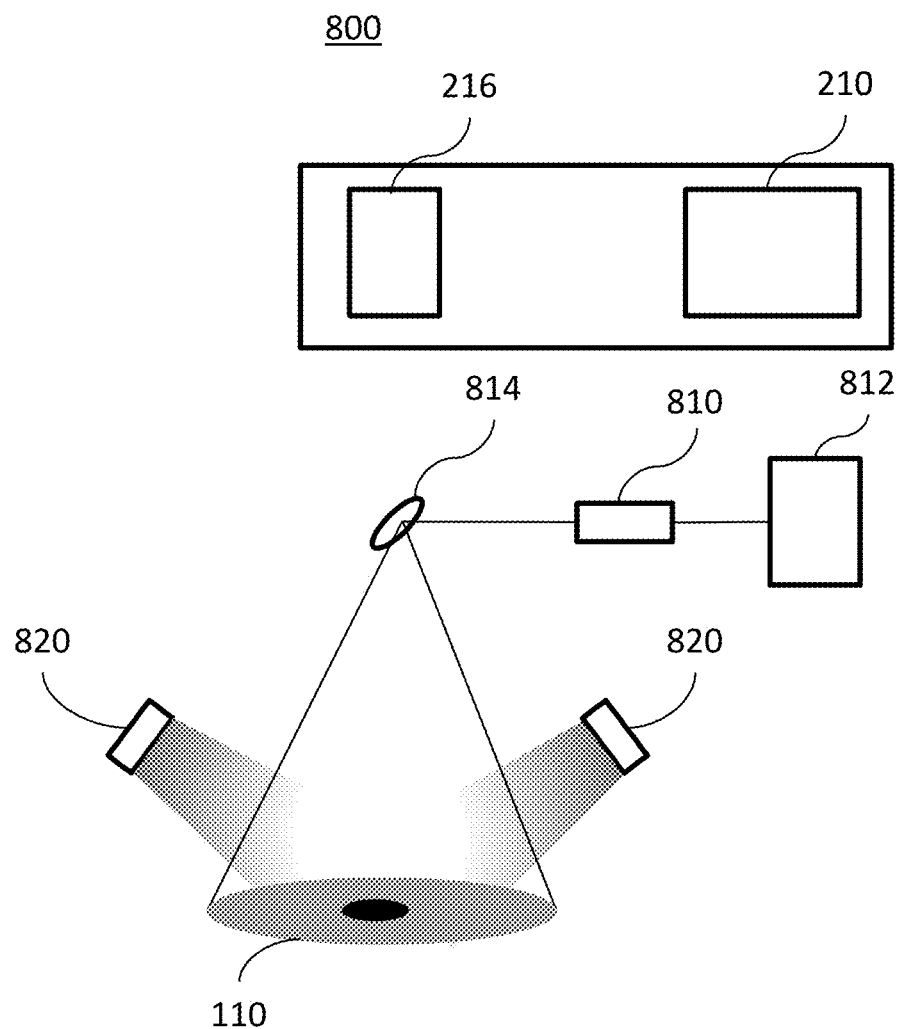
FIG. 8 shows a simplified diagram of a system having laser system and image sensor for use in rangefinding in accordance with one or more embodiments.

FIG. 8 shows a simplified diagram of a system 800 having laser system 210 and image sensor 810 for use in rangefinding in accordance with one or more embodiments. In conjunction with any of the patient support systems disclosed herein, the rangefinder may be utilized for accurately locating the eye, and in particular, the location of the iris stroma for the proper delivery of focused laser light. The rangefinder may include an image sensor that receives optical information about the patient and/or eye and utilizes this information to determine the distance and/or orientation of the eye relative to a reference point. To address the above problem, some implementations of the disclosed methods may include imaging the iris with an image sensor operatively connected to a computer 812. Examples of image sensors may include an infrared camera used in conjunction with infrared illumination sources 820. In some embodiments, optical data (e.g., light reflected from the eye) may be directed to the image sensor via dichroic mirror 814.

Some implementations of the disclosed methods may include utilizing a rangefinder as part of the optical tracking system to provide accurate distances to the target location in the eye. For example, the rangefinder may determine a distance between the iris and a reference component of the optical tracking system. Examples of reference components may include the last optical component in the laser system (e.g., a window or lens closest to the patient), a mirror or galvos, or any other component or location in the laser system with a known location to provide a point of reference for the rangefinding.

Based on the determined distance, the system may control the focal point of the laser beam to remain substantially in focus between an anterior surface and posterior surface of the iris, at the stromal pigment targeted for removal, or at any of the disclosed possible focusing planes. Examples of rangefinders may include, for example, triangulation lasers, time of flight detectors, phase shift detectors, ultrasonic detectors, frequency modulation detectors, interferometers, a camera, or a light sensor.

Triangulation may utilize lasers for distance measurements. Structural embodiments of exemplary triangulation methods may include three elements: an imaging device, an illumination source, and either an additional imaging device or an additional illumination source. Illumination source(s) may include image projectors that project light images onto the iris, sclera, or other patient field. Exemplary light images might include circles and lines. In one embodiment, the laser beam may illuminate a point on the surface of the target (e.g., the iris, the sclera, or some other point on the patient's face). Diffuse or specular reflections from the illuminated point may be monitored with a position-sensitive detector, which may be placed a given distance from the laser source such that the laser source, the target point, and the detector form a triangle. Assuming the beam incidence angle to the target is 0°, the position-sensitive detector identifies the incidence angle of the detector to the target, and the distance between the laser source and the detector is known, the distance from the laser source to the target may be determined with the appropriate trigonometric function.

Time-of-flight or pulse measurements may measure the time of flight of a radiation pulse from the measurement device to the target and back again. Exemplary forms of radiation include light (e.g., near-infrared laser) and ultrasound. An exemplary time-of-flight apparatus includes a radiation source, a radiation sensor, and a timer. Time of flight may be measured based upon timed pulses or the phase shift of an amplitude modulated wave. In the case of timed pulses, the speed of the radiation is already known, so the timer measures the turnaround time of each pulse to determine the distance, where distance=(speed of radiation×time of flight)/2.

The phase shift method may utilize an intensity-modulated laser beam. The phase shift of intensity modulation may be related to the time of flight. Compared with interferometric techniques, its accuracy is lower, but it allows unambiguous measurements over larger distances and is more suitable for targets with diffuse reflection. For small distances, ultrasonic time-of-flight methods may be used, and the device may contain an aiming laser for establishing the direction of the ultrasonic sensor, but not for the distance measurement itself.

Frequency modulation methods may include frequency-modulated laser beams, for example with a repetitive linear frequency ramp. The distance to be measured may be translated into a frequency offset, which may be measured via a beat note of the transmitted and received beam.

Interferometers may be implemented for distance measurements with an accuracy which is far better than the wavelength of the light used.

Various systems for rangefinding may provide very accurate measurements, for example, determining distances with the resolution of at least 10, 200, 500, or 750 μm. Such systems may include, for example, a time-domain optical coherence tomography system, a spectral domain optical coherence tomography system.

Utilizing the disclosed rangefinding, some methods may utilize the same structure to include autofocusing the laser system in response to changes in the determined distance and corresponding shifts in the focal point of the beam. Computer systems in communication with the laser system may automatically autofocus the laser system and measure a distance to the stromal pigment of the iris at periodic intervals (e.g., at approximately 1 kHz, 10 kHz, 100 kHz, etc.).

Exemplary methods for lens focusing include manually or electronically (a) shifting the position of one or more focal lenses (e.g., a lens mounted on a motor stage to shift along the beam access), (b) shifting the position of one or more focal mirrors (e.g., by adding a third mirror to a galvos beam steering system), (c) changing the shape of one or more focal lenses or mirrors, (d) deflecting or refracting a beam by means of an acousto-optical or electro-optical devices, or (e) using electrostatic or electromagnetic lenses or mirrors to shift the focal position of the beam.

Movement of the patient's head and eyes along the z axis can frustrate accurate rangefinding and autofocusing. By positioning the patient such that the head is supported and the neck muscles are permitted to release, z head position changes may be minimized.

Topographical variations in the anterior iris surface may also frustrate accurate rangefinding and autofocusing. These variations result primarily from three elements: iris tilt, iris folds, and iris crypts. Iris tilt is a naturally occurring phenomenon. As a result, the iris plane will rarely reside perpendicular to the beam axis. The iris plane tilts about both its the horizontal and vertical axes, and can tilt as much as 5°, which results in z variations of up to 700 μm from one edge of the iris to the other (assuming a roughly 11 mm horizontal iris diameter). An iris tilt system may be utilized to significantly reduce or eliminate this iris surface variation.

Iris folds are also a naturally occurring phenomenon. As the iris dilates, it folds like a drape, concentric to and away from the pupil. These folds can create significant z variations in the iris topography. To significantly reduce or eliminate iris folds, some methods may include introduction of a topical miotic solution, such as Pilocarpine ophthalmic solution. In one embodiment, patents may be dosed with 1 drop of 2% Pilocarpine ophthalmic solution 15, 10, and 5 minutes prior to the procedure to achieve high miosis, resistant to the potentially dilative effect of lasing the iris anterior to the iris dilator muscles during the procedure. Each patient may also be given 500 mg of acetaminophen (orally) 30 minutes prior to the procedure as a prophylaxis against headaches from ciliary body tension.

Iris crypts are another common phenomenon. They are created by spaces between the iris stromal fibers. In brown eyes, these crypts are typically filled with pigment and can therefore be ignored for purposes of the initial treatment sessions. Once the stromal pigment has been substantially eliminated outside of the crypts, stromal pigment might remain in the depths of the iris crypts. Pigment spots occur naturally in light eyes, so this remaining crypt pigment should not look unnatural and should barely be noticeable.

If remaining pigment spots bother the patient, the system can remove or reduce the remaining crypt pigment by slightly shifting the beam waist posteriorly into the stroma and rescanning the iris using this shifted waist position. This shifted waist setting may also be an option displayed for selection by the operator on the touch screen interface. The distance of the shift of the beam waist may be equal to about 80% of the beam DOF to ensure delivery of high fluence within the pigmented crypts. If the crypt pigment remains 3-4 weeks after treatment with this posterior waist shift, this waist shift procedure may be repeated, posteriorly shifting the beam waist each time by another 80% of the DOF, until the crypt pigment is eliminated sufficiently eliminated.

Figure 8A:
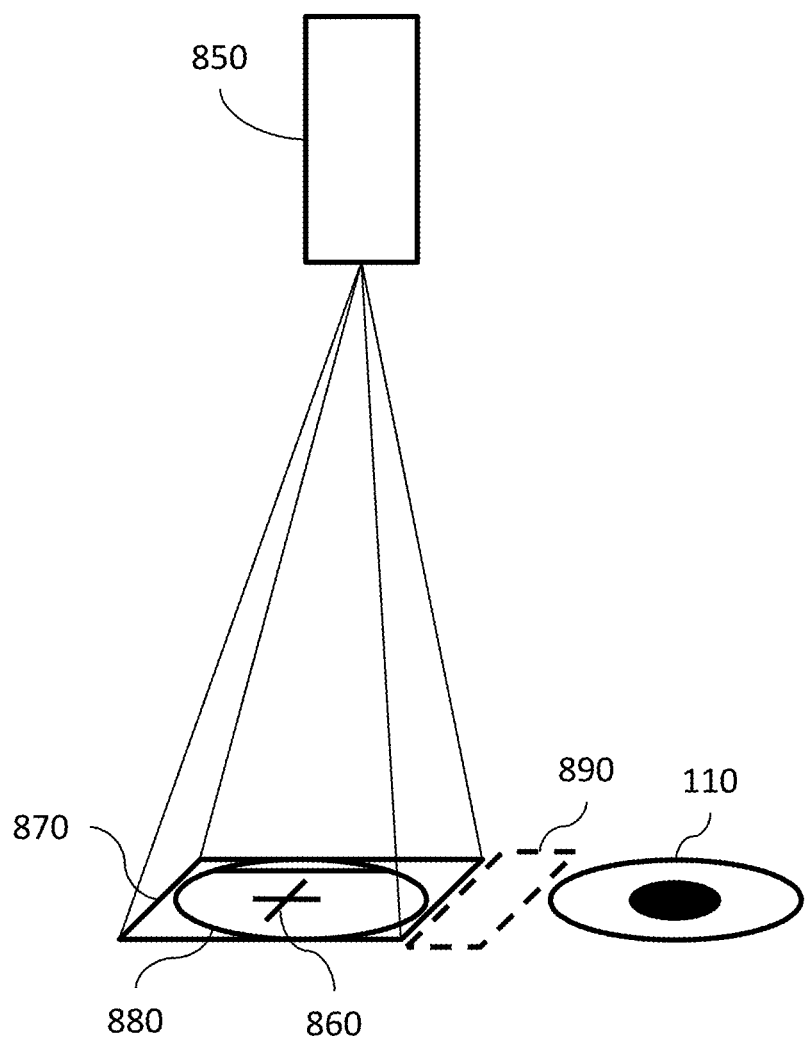
FIG. 8A shows a simplified diagram of a rangefinder configured for performing coarse resolution measurements in accordance with one or more embodiments.
Figure 8B:
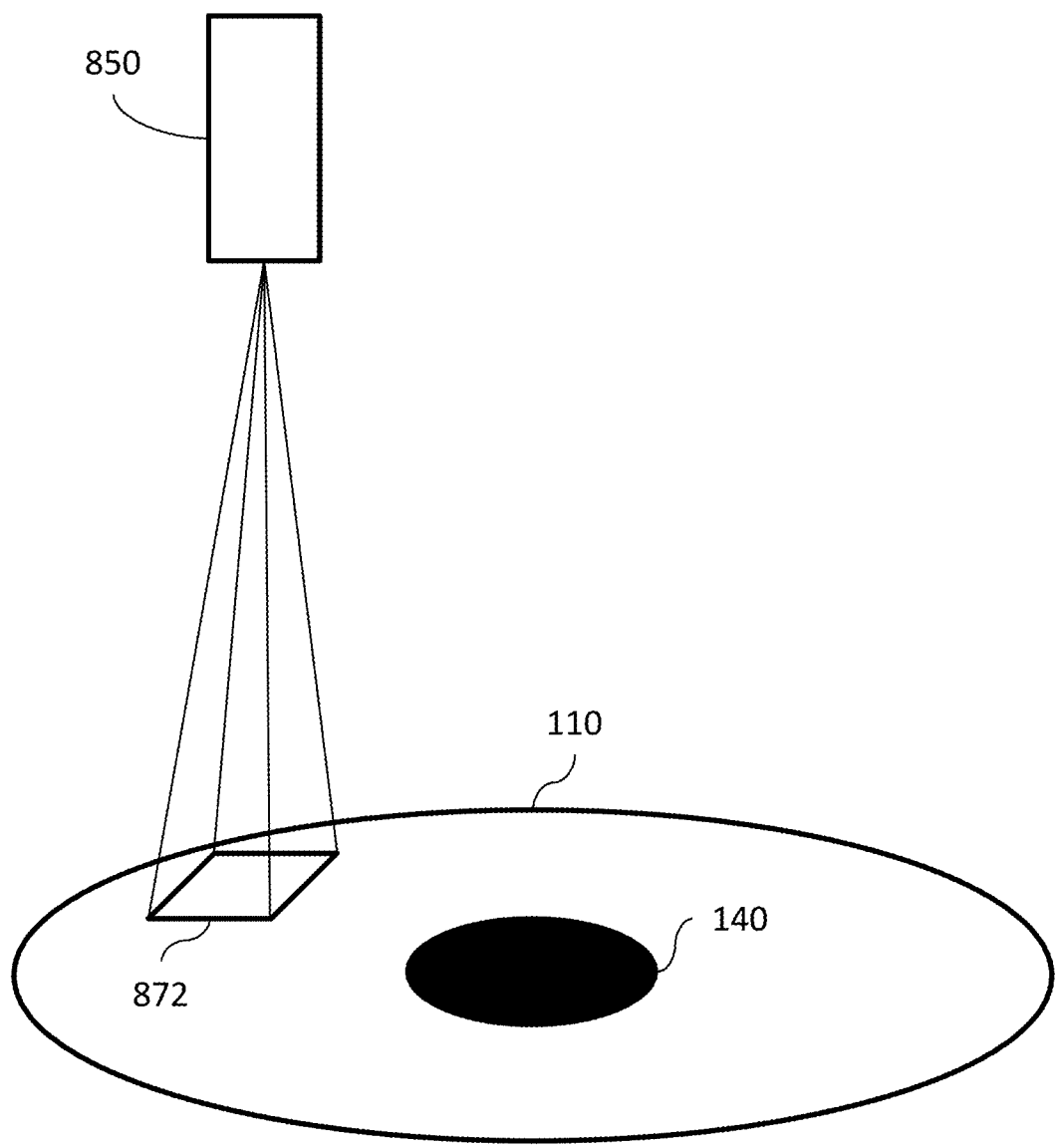
FIG. 8B shows a simplified diagram of a rangefinder configured for performing fine resolution measurements in accordance with one or more embodiments.

FIGS. 8A and 8B show simplified diagrams of a rangefinder configured for performing coarse and/or fine resolution measurements in accordance with one or more embodiments. A challenge with conventional patient support systems that are integrated into treatment systems is how to efficiently position a patient utilizing available rangefinding or positioning systems. Inefficient systems may be prone to patient positioning error, slow operation, delays in treating multiple patients, or undue wear on mechanical systems such as by using fine adjustment hardware for what should be a coarse patient adjustment.

As shown in FIG. 8A, the disclosed systems may include a rangefinder 850 configured to have multiple resolutions for use when positioning a patient with the patient support structure, which also has multiple resolutions in patient positioning. For example, the rangefinder can be configured to be set to a coarse resolution for determining the distance for a coarse adjustment of the patient support structure or a fine resolution for determining the distance for a fine adjustment of the patient support structure. In various embodiments, the coarse resolution of the rangefinder may be between 2000 microns and 6000 microns and the fine resolution may be between 5 microns to 2000 microns, with other ranges contemplated as within the scope of the present disclosure. Thus, in certain embodiments, the coarse resolution is larger than the fine resolution. As used herein, the term "resolution" (with reference to a rangefinder) refers to the smallest window of a distance measurement that the rangefinder is able to resolve at its current setting. For example, if the resolution was 3000 microns, then any given distance measurement would have a window of uncertainty of approximately 1500 microns on either side of the reported distance measurement. A corresponding definition is applied to the "resolution" of the patient support structure, e.g., as described previously, one may have a coarse resolution of 1 cm and a fine resolution of 1 mm.

The present disclosure contemplates embodiments where the coarse and fine adjustment hardware may be utilized for manual operation, based on the resolution set on the rangefinder and optionally in conjunction with the generation of "indications" of patient position to aid the user in positioning the patient. In one embodiment, the coarse adjustment hardware may be configured to be manually operated to perform a coarse adjustment based on the resolution set on the rangefinder. Optionally, the system may be configured to generate, during the coarse adjustment, an indication of the position of the anterior iris relative to a target position of the anterior iris. As used herein, an "indication" refers to an audio, visual, haptic, or other human-detectable feedback mechanism that indicates information about the measured distance relative to a target distance (i.e., where the system is trying to locate the eye anatomy for treatment). For example, as depicted in FIG. 8A, the indication 860 may be a crosshair projected onto the patient. Other embodiments of indications may include sounds, a series of lights (e.g., green then yellow then red), displays at a monitor of an image of the patient (actual or animated), or calibration markers showing the patient's proximity to the desired Z position of, for example, the patient's anterior iris surface to perform the procedure on that iris. Such indications may also be generated in conjunction with the system performing X-Y alignment.

Other variations are contemplated for embodiments where the coarse adjustment hardware may be configured to be automatic to perform a coarse adjustment based on the resolution set on the rangefinder. Also, the system may be configured to generate, during the coarse adjustment, an indication of the position of the anterior iris relative to a target position of the anterior iris. In such variations, the system may be configured to allow a user to initiate an automatic coarse adjustment after which the computing systems associated with the rangefinder and the patient support structure perform the adjustment. Yet another embodiment is where the coarse adjustment hardware may be configured to be automatic and the system may be configured to automatically perform a coarse adjustment, or portion thereof, based on the resolution set on the rangefinder. While the above features (manual/automatic operation, indication generation, etc.) are described with reference to a coarse adjustment, such may also be performed substantially similarly with the disclosed fine or ultra-fine adjustments described herein.

Also depicted in FIG. 8A is an "area of interest," which as used herein, means an area on the patient where one point (e.g., an endpoint) of the determined distance is calculated to. FIG. 8A particularly shows one example for an area of interest 870 for a coarse adjustment. In this embodiment, the area of interest is an area surrounding a closed eyelid 880 of the patient. As such, in this example, the distance can be calculated from anywhere on the closed eyelid to the reference point in the rangefinder. For example, the point on the eyelid may correspond to the center of the illustrated indication (cross-hair), a point midway between the cross-hair and the edge of the area of interest, etc. Other possible areas of interest can be, for example, the nasal bridge 890 (depicted in FIG. 8A), a forehead, or other part of the patient's anatomy suitable for providing a known reference point having a generally known distance relationship to the iris. For example, the Z position of the highest point on the anterior surface of the nasal bridge might be 1.2-2.5 cm from the Z position of the anterior surface of the patient iris, and the Z position of the highest point on the anterior surface of the treatment eyelid might be between 2.5-5.0 mm from the Z position of the anterior surface of the patient iris. This data may reside in computer memory and accounted for when analyzing the coarse Z measurements and predicting the Z position of the anterior surface of the iris for fine adjustments. Exemplary sizes of the areas of interest may be 10×10 cm, 5×5 cm, 2×3 cm, 1×1 cm, etc., with appropriate numerical areas based on the shape of the area. The area of interest may be any shape, e.g., square, rectangular, oval, or irregular. The area of interest need not be contiguous and may comprise a number of areas having exemplary total areas as given above.

In various embodiments, the rangefinder may also be configured to be set to a fine resolution and the distance being in an area of interest as described above. In certain embodiments, such as when the rangefinder is set to the fine resolution, the area of interest may be smaller than that when the rangefinder is set to the coarse resolution. FIG. 8B illustrates such an embodiment. Here, the area of interest 872 is a portion of the patient's iris 110. For fine adjustments, the area of interest may typically be smaller, for example, 10×10 mm, 5×5 mm, 2×3 mm, 1×1 mm, etc. The area of interest 872 may also be in other locations, such as outside the pupil, adjacent the eye, at the fundus (e.g., where the measurement point is made through the pupil to maintain approximate centering of the area of interest), etc.

Additionally, the system may be further configured to provide what is referred to herein as "ultra-fine" adjustments. Such ultra-fine adjustments may be undertaken to very precisely position the patient so the focal plane of the laser is as close as possible to the target pigment. Such ultra-fine adjustments may be performed after the patient support structure has performed coarse and/or fine adjustments. For example, the rangefinder may be configured to be set to a coarse resolution or a fine resolution. The system may be configured to perform a coarse adjustment of the patient support surface utilizing the coarse adjustment hardware and perform a fine adjustment of the patient support surface utilizing the fine adjustment hardware. Additionally, the system may be configured to perform an ultra-fine adjustment of an element of the laser system. In some embodiments, the element may be a lens of the laser system (e.g., a lens in optical exit 220), a mirror, laser hardware controlling beam divergence, etc. In one example, performing the ultra-fine adjustment may include the system adjusting a position of a lens to reduce a difference between a target distance and the distance as determined by the rangefinder. For example, this may include moving a third galvos axis (e.g., controlling a Z shift) or the moving a lens mounted on a motor stage. In some embodiments, the system may be configured to perform the ultra-fine adjustment with a resolution of 5 microns or less.

One example of a method for one of the disclosed embodiments may include the system initiating a Z-alignment procedure. The system may then perform a coarse adjustment (rangefinder resolution 3000 microns, area of interest 2×3 cm, patient support structure moves with a 2 cm resolution (or steps)). The system's computer finds and causes the best patient support structure position for the coarse setting (so the focal point or plane is within a best 2 cm window—limited by patient support structure).

Then, the system may switch to fine adjustment (rangefinder resolution 15 microns, area of interest 1×1 mm, patient support structure moves in with a 10 mm resolution (or steps)). After the fine adjustment, the focal point is in a 10 mm window—again limited to resolution of support movement.

After the fine adjustment, an ultra-fine adjustment may be performed by moving a lens to bring the focal plane as close as possible to a target position in 5 micron steps—but now limited by, e.g., the 15 micron resolution of the rangefinder.

Figure 9:
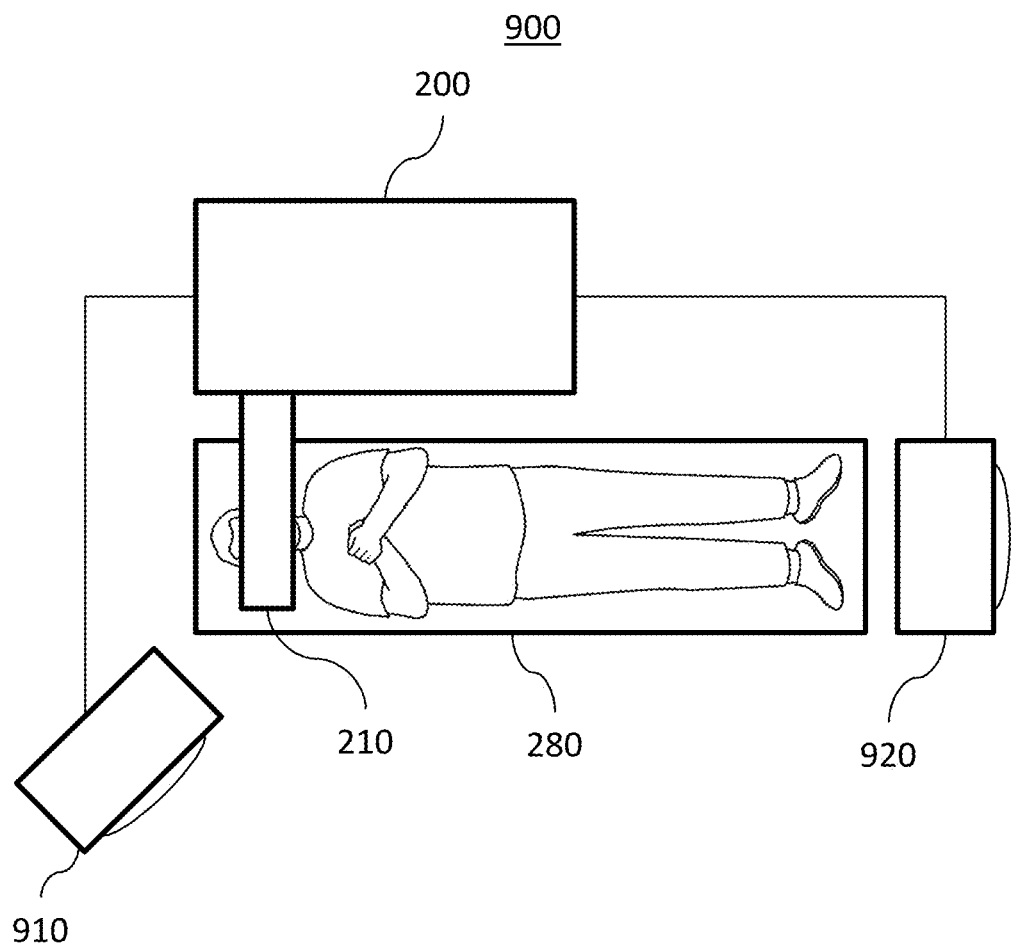
FIG. 9 shows a simplified system including detached physician and technician consoles in accordance with one or more embodiments.

FIG. 9 shows a simplified system 900 including detached physician 910 and technician 920 consoles in accordance with one or more embodiments. To allow for control of the procedure, some embodiments of the present disclosure may have physician console 910 in communication (e.g., wired or wirelessly) with the laser system and physically detached (but allowing for wired connections) from the laser system. The physician console may be configured to display patient data including one or more of patient images, patient medical record data, or patient treatment data associated with the color alteration procedure performed by the laser system. In addition to monitoring data at the physician console, the physician console may also be configured to accept input that controls the laser system and/or the patient support surface. Exemplary advantages of the detached aspect of the physician console may include permitting the physician to have freedom of movement about the treatment area while still being able to directly control the procedure. In the example shown in FIG. 9, the physician may be located near the patient's head to facilitate communication with the patient as well as to be in the most optimal position for directly monitoring the procedure. As used herein, the term "physically detached" means that the console is not rigidly mounted to the laser system or patient support structure. For embodiments with wireless connectivity, the consoles may be completely lacking physical connection to the above. For embodiments with wired connectivity, there may be flexible wires or cables connecting them to the above, but still allowing substantial freedom to the user of the console. The present disclosure also contemplates other embodiments where the console may not be "physically detached" as described above, but may be located on an articulated arm (which may or may not be connected to laser system or patient support structure) and thus allow substantially independent position of the console.

Also shown in FIG. 9 is an example of a technician console 920. Here, the technician console is shown positioned near the feet of the patient, for example to not interfere with the physician or to monitor the patient at a different angle to see things during the procedure that the physician may not be able to. Also, the technician console may allow the technician to be at needed locations proximate the patient for the delivery of other treatment, for example, injections, monitoring blood pressure, etc. In some embodiments, the technician console, similar to the physician console above, may be in communication with the laser system but physically detached from the laser system and the physician console. In this way, some embodiments may provide the maximum freedom for the physician and the technician to be at the optimal locations during treatment.

In the context of the present disclosure, which describes embodiments of systems for an eye color alteration procedure, the physician console and the technician console may be configured to be in communication to view real-time images and the patient treatment data associated with the color alteration procedure. In some embodiments, the physician console may be configured to override commands for the laser system that were initiated by the technician console. For example, the commands issued from the physician console may override those from the technician console, but the reverse may not be true. In this way, in situations where there may be a conflict between commands from the physician console and the technician console, the physician console has preference.

Figure 10:
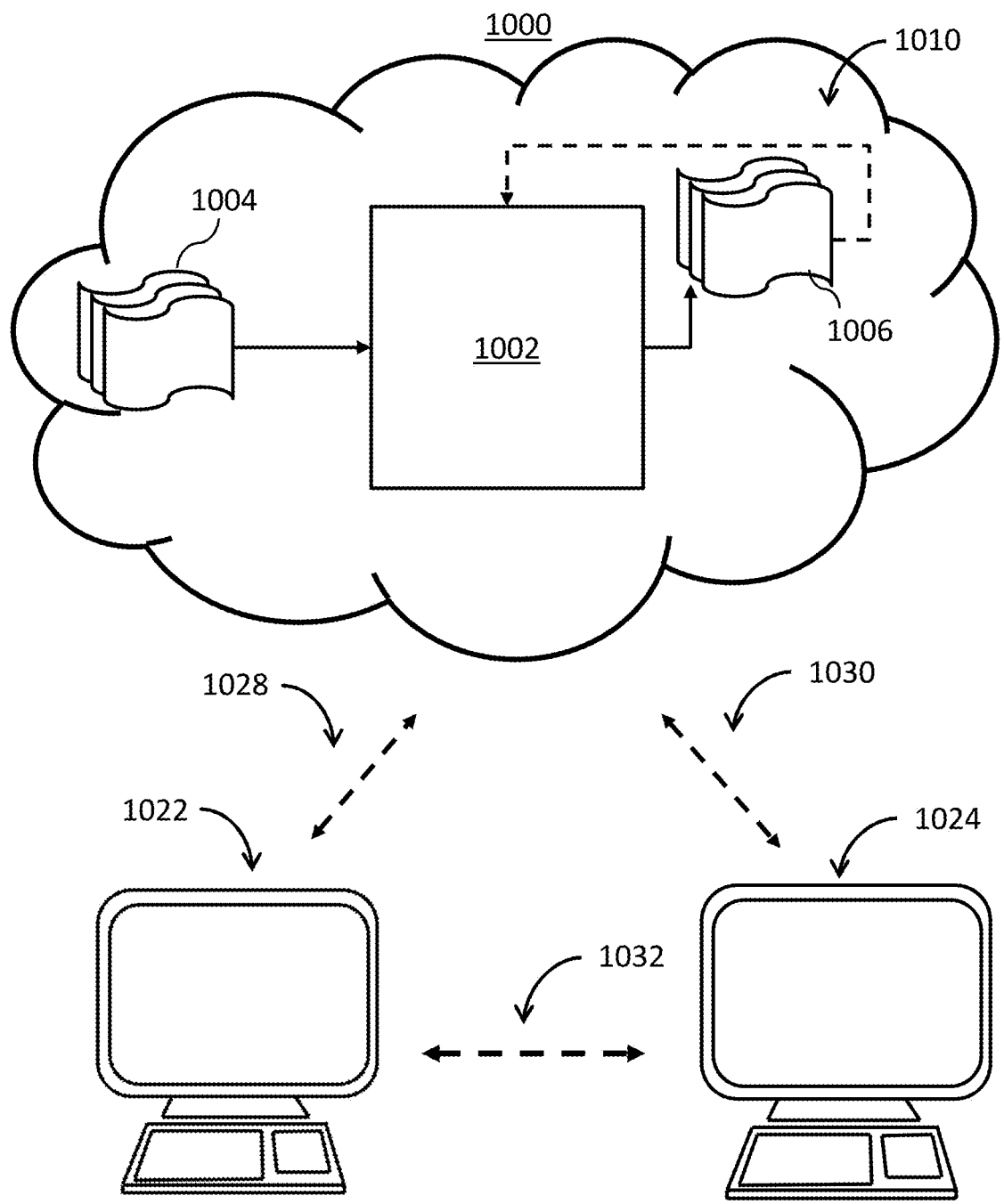
FIG. 10 shows an illustrative system for performing an eye color changing procedure in accordance with one or more embodiments.

FIG. 10 shows an illustrative system for performing an eye color changing procedure in accordance with one or more embodiments. For example, system 1000 may represent the components used for performing an eye color changing procedure. For example, system 1000 may power a local device to perform an eye color changing procedure where the required determination (e.g., iris mapping, pattern to follow, laser power to deliver, identification of patient, alignment of patient, etc.) are determined remotely and/or in the cloud. As shown in FIG. 10, system 1000 may include user terminal 1022 and user terminal 1024. While shown as personal computers, in FIG. 10, it should be noted that user terminal 1022 and user terminal 1024 may be any computing device, including, but not limited to, a laptop computer, a tablet computer, a hand-held computer, other computer equipment (e.g., a server), including "smart," wireless, wearable, and/or mobile devices. FIG. 10 also includes cloud components 1010. Cloud components 1010 may alternatively be any computing device as described above and may include any type of mobile terminal, fixed terminal, or other device. For example, cloud components 1010 may be implemented as a cloud computing system and may feature one or more component devices. It should also be noted that system 1000 is not limited to three devices. Users may, for instance, utilize one or more other devices to interact with one another, one or more servers, or other components of system 1000. It should be noted that, while one or more operations are described herein as being performed by particular components of system 1000, those operations may, in some embodiments, be performed by other components of system 1000. As an example, while one or more operations are described herein as being performed by components of user terminal 1022, those operations may, in some embodiments, be performed by components of cloud components 1010. In some embodiments, the various computers and systems described herein may include one or more computing devices that are programmed to perform the described functions. Additionally, or alternatively, multiple users may interact with system 1000 and/or one or more components of system 1000. For example, in one embodiment, a first user and a second user (e.g., a technician and a physician) may interact with system 1000 using two different components.

With respect to the components of user terminal 1022, user terminal 1024, and cloud components 1010, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing circuitry. Each of these devices may also include a user input interface and/or user output interface (e.g., a display) for use in receiving and displaying data. For example, as shown in FIG. 10, both user terminal 1022 and user terminal 1024 include a display upon which to display data (e.g., information related to an eye color changing procedure).

Additionally, as user terminal 1022 and user terminal 1024 are shown as touchscreen smartphones, these displays also act as user input interfaces. It should be noted that in some embodiments, the devices may have neither user input interface nor displays and may instead receive and display content using another device (e.g., a dedicated display device such as a computer screen and/or a dedicated input device such as a remote control, mouse, voice input, etc.). Additionally, the devices in system 1000 may run an application (or another suitable program). The application may cause the processors and/or control circuitry to perform operations related to an eye color changing procedure.

Each of these devices may also include electronic storages. The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information obtained from servers, information obtained from client devices, or other information that enables the functionality as described herein.

FIG. 10 also includes communication paths 1028, 1030, and 1032. Communication paths 1028, 1030, and 1032 may include the Internet, a mobile phone network, a mobile voice or data network (e.g., a 10G or LTE network), a cable network, a public switched telephone network, or other types of communications network or combinations of communications networks. Communication paths 1028, 1030, and 1032 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Cloud components 1010 may be a database configured to store user data for a user. For example, the database may include user data that the system has collected about the user through prior operations and/or procedures. Alternatively, or additionally, the system may act as a clearing house for multiple sources of information about the user. Cloud components 1010 may also include control circuitry configured to perform the various operations needed to perform an eye color changing procedure.

Cloud components 1010 include machine learning model 1002. Machine learning model 1002 may take inputs 1004 and provide outputs 1006. The inputs may include multiple data sets such as a training data set and a test data set. Each of the plurality of data sets (e.g., inputs 1004) may include data subsets related to user data, an eye color changing procedure, patient progress, and/or results. In some embodiments, outputs 1006 may be fed back to machine learning model 1002 as input to train machine learning model 1002 (e.g., alone or in conjunction with user indications of the accuracy of outputs 1006, labels associated with the inputs, or with other reference feedback information). In another embodiment, machine learning model 1002 may update its configurations (e.g., weights, biases, or other parameters) based on the assessment of its prediction (e.g., outputs 1006) and reference feedback information (e.g., indication of accuracy, results of procedure, reference labels, and/or other information). In another embodiment, where machine learning model 1002 is a neural network, connection weights may be adjusted to reconcile differences between the neural network's prediction and the reference feedback. In a further use case, one or more neurons (or nodes) of the neural network may require that their respective errors are sent backward through the neural network to facilitate the update process (e.g., backpropagation of error). Updates to the connection weights may, for example, be reflective of the magnitude of error propagated backward after a forward pass has been completed. In this way, for example, the machine learning model 1002 may be trained to generate better predictions (e.g., predictions related to an appropriate iris mapping to use, pattern to follow, laser power, level of eye color change, number of procedures, length of procedures, etc.

In some embodiments, machine learning model 1002 may include an artificial neural network. In such embodiments, machine learning model 1002 may include an input layer and one or more hidden layers. Each neural unit of machine learning model 1002 may be connected with many other neural units of machine learning model 1002. Such connections may be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Machine learning model 1002 may be self-learning and trained, rather than explicitly programmed, and may perform significantly better in certain areas of problem solving, as compared to traditional computer programs. During training, an output layer of machine learning model 1002 may correspond to a classification of machine learning model 1002 and an input known to correspond to that classification may be input into an input layer of machine learning model 1002 during training. During testing, an input without a known classification may be input into the input layer, and a determined classification may be output.

In some embodiments, machine learning model 1002 may include multiple layers (e.g., where a signal path traverses from front layers to back layers). In some embodiments, back propagation techniques may be utilized by machine learning model 1002 where forward stimulation is used to reset weights on the "front" neural units. In some embodiments, stimulation and inhibition for machine learning model 1002 may be more free flowing, with connections interacting in a more chaotic and complex fashion. During testing, an output layer of machine learning model 1002 may indicate whether or not a given input corresponds to a classification of machine learning model 1002 (e.g., an eye color change requested, a pattern to follow, a laser power to deliver, alignment of patient, etc.).

Figure 11:
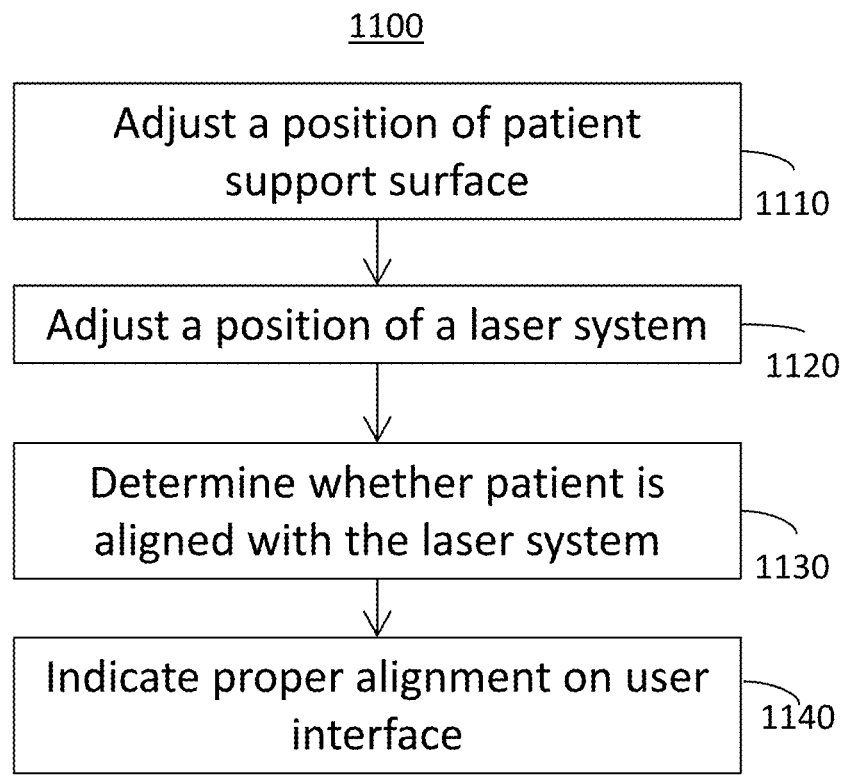
FIG. 11 shows a process for supporting and aligning a patient during a color alteration procedure in accordance with one or more embodiments.

FIG. 11 shows a process for supporting and aligning a patient during a color alteration procedure in accordance with one or more embodiments. For example, process 1200 (e.g., via one or more components of FIGS. 2-10) may represent the steps taken by one or more devices as shown in FIGS. 2 and 8 ahead of or during an eye color changing procedure. For example, the system may need to align a patient with a laser system prior to a procedure. Furthermore, the system may need to ensure the patient is aligned and the patient's neck muscles are not engaged (e.g., to prevent head movement during a procedure).

At step 1110, process 1100 (e.g., via one or more components of FIGS. 2-10) adjust a position of patient support surface. For example, in order to prevent head movement, the patient support surface may comprise a surface extending in a direction that is substantially perpendicular to a direction of a laser delivered from the laser system. To ensure alignment before, during, and/or after (e.g., in order to allow a patient to exit) the procedure, the support structure may be adjustable (e.g., via controls entered into a user interface of a computer system and/or through manual adjustment through mechanical means) to set a patient position or alignment relative to the laser system. For example, the system may adjust the position of the support structure using course and fine adjustment hardware.

At step 1120, process 1100 (e.g., via one or more components of FIGS. 2-10) adjust a position of patient support surface. For example, additionally or alternatively to the adjustment of the patient support surface, the system may also adjust a position of the laser system. For example, the system may adjust the position of the laser system to ensure that using one or more automatic and/or manual adjustment means. In some embodiments, the adjustment of the laser system may include adjustments based on information from optical tracking systems and/or rangefinder systems. For example, before and/or during the procedure the system may automatically adjust the laser system in order to perform the eye color procedure.

At step 1130, process 1100 (e.g., via one or more components of FIGS. 2-10) determine whether a patient is aligned with the laser system. For example, the system may first automatically determine that a patient is in a correct location and/or has a correct location before continuing with the process. In some embodiments, the determination may be based on the direction of laser light and a position of an iris of the user (e.g., as described in FIGS. 1-2).

At step 1140, process 1100 (e.g., via one or more components of FIGS. 2-10) indicates proper alignment on a user interface. For example, the system may generate one or more notifications (e.g., on a user interface for physician 910 and technician 920 as shown in FIG. 9). In response to, or in additional to, the system generating the notification, the system may enable the procedure to continue.

Figure 12:
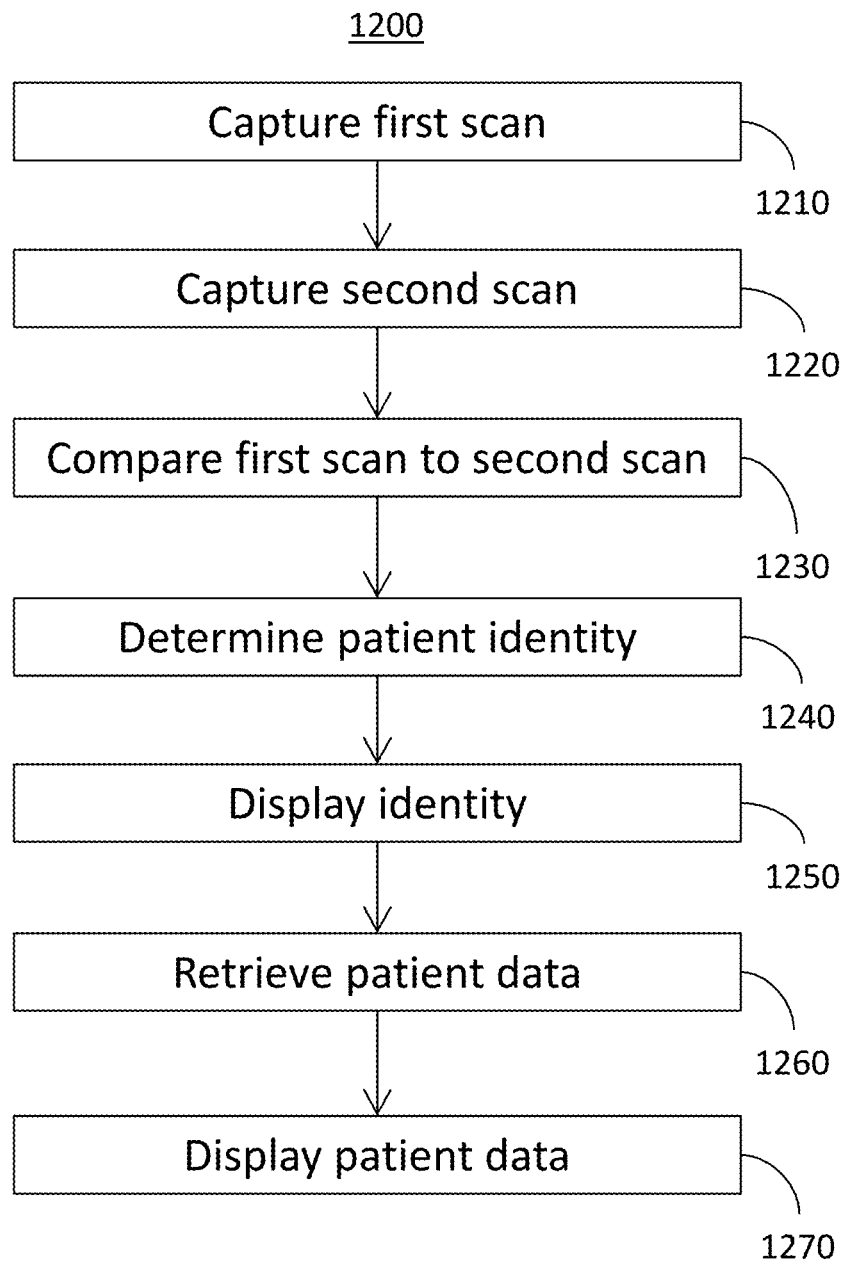
FIG. 12 shows a process for allowing the performance of an eye color changing procedure in accordance with one or more embodiments.

FIG. 12 shows a process for allowing the performance of an eye color changing procedure in accordance with one or more embodiments. In some embodiments, the system may also include an image sensor to acquire a scan of the patient's iris or retina. Such scans may be utilized to ensure patient identity and/or a proper medical condition prior to the beginning of an eye color alteration procedure, with the patient data displayed for the physician. For example, process 1200 (e.g., via one or more components of FIGS. 2-10) may represent the steps taken by one or more devices as shown in FIGS. 2 and 8 ahead of or during an eye color changing procedure.

At step 1210, process 1200 (e.g., via one or more components of FIGS. 2-10) captures a first scan. For example, an image sensor may capture the first scan at a first time prior to the altering of the eye color. The first scan may be of at least one of an iris or retina of the patient.

At step 1220, process 1200 (e.g., via one or more components of FIGS. 2-10) captures a second scan with the image sensor and at a second time later than the first time and prior to the altering of the eye color, the second scan being of at least one of the iris or the retina of the patient. For example, the first scan may be done as part of a consultation exam or other pre-procedure scan. The second scan may, for example, be taken shortly before the procedure or even at the start of the procedure to confirm the identity of the patient as described in the next steps.

At step 1230, process 1200 (e.g., via one or more components of FIGS. 2-10) compares the first scan captured at the first time with the second scan captured at the second time. Software as described in FIG. 10 may perform the comparison. For example, the machine learning algorithms may be trained from a patient library of iris patterns and/or retinal patterns (e.g., which may contain the first scan) to recognize the patterns of a particular patient.

At step 1240, process 1200 may (e.g., via one or more components of FIGS. 2-10) determine an identity of the patient based on matching the first scan captured at the first time with the second scan captured at the second time. For example, the trained algorithm described above may use the second scan as input and determine the identity of the patient and/or a confidence value of a match.

At step 1250, process 1200 may (e.g., via one or more components of FIGS. 2-10) generate, for display on a user interface, a confirmation of the identity of the patient. The confirmation may be in the form of graphical and/or textual output at the display. The confirmation may include, for example, a patient's name, medical record number, or other personal identifying information.

At step 1260, process 1200 may (e.g., via one or more components of FIGS. 2-10) retrieve patient medical record data based on the first scan or the second scan. For example, medical databases may be accessed via the networked computing systems disclosed in FIG. 10. With the confirmed identity, such access may be more readily obtained from secure medical record databases. For example, in some embodiments, the patient medical record data may include a treatment plan for delivery by the laser system.

At step 1270, process 1200 (e.g., via one or more components of FIGS. 2-10) displays, at the physician console, the patient medical record data based on the iris scan. Similar to step 1260, the patient medical record data may be in the form of textual and/or graphical information representative of the patient's medical records. This may include, for example, the patient's current or past medical condition, information about past and/or the current color alteration procedure, etc. Accordingly, in some embodiments, the system may enable the laser system to deliver the treatment plan based on the first scan or the second scan corresponding to patient identification included with the patient medical record data.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

Embodiment 1: A system for supporting and aligning a patient during a color alteration procedure, the system comprising: a laser system for performing the color alteration procedure, wherein the laser system delivers a laser in a first direction; a control computer system adjacent to the laser system for controlling the laser system during the color alteration procedure, the control computer system comprising a user interface in a first plane substantially perpendicular to the first direction; and a patient support structure comprising: a patient support surface extending in a second direction that is substantially perpendicular to the first direction and configured to be adjustable to set a patient position or alignment relative to the laser system; coarse adjustment hardware configured to cause automated and/or manual adjustments to the patient support surface in the first direction; and fine adjustment hardware configured to cause automated fine adjustments to the patient support surface in the first direction based on instructions received from the control computer.

Embodiment 2: The system of any of the preceding embodiments, the patient support structure comprising a head support element configured to cause a head of the patient to be supported without engagement of neck muscles.

Embodiment 3: The system of any of the preceding embodiments, the patient support structure comprising a lower support portion and an upper reclining portion, the head support element mounted to the upper reclining portion and the head support element is adjustable to set the patient position or alignment.

Embodiment 4: The system of any of the preceding embodiments, the patient support surface further comprising an adjustable leg portion mounted to the lower support portion.

Embodiment 5: The system of any of the preceding embodiments, the head support element comprising an aperture in the patient support surface, the head support element is configured to support the head with the patient in a face-down position on the patient support surface and the aperture allowing access to the eye.

Embodiment 6: The system of any of the preceding embodiments, the patient support structure comprising an adjustable seat configured to move in the first direction relative to the head support element such that the movement changes the tilt of the eye when the head is resting on the head support element.

Embodiment 7: The system of any of the preceding embodiments, wherein the coarse adjustment hardware is further configured to move the patient support surface substantially perpendicular to the first direction.

Embodiment 8: The system of any of the preceding embodiments, the coarse adjustment hardware being a manual adjustment system that is configured to adjust the patient position to be in a direction substantially parallel to an optical axis of the laser system.

Embodiment 9: The system of any of the preceding embodiments, the fine adjustment hardware comprising a hydraulic system configured to cause adjustment of the patient support surface with a resolution of 10 millimeters or less.

Embodiment 10: The system of any of the preceding embodiments, wherein fine adjustments utilizing the fine adjustment hardware are performed automatically by the system based on a treatment plan for altering an eye color of the patient.

Embodiment 11: The system of any of the preceding embodiments, further comprising an optical tracking system includes a rangefinder, the method further comprising determining, utilizing the rangefinder, a distance between the iris and a reference component of the optical tracking system.

Embodiment 12: The system of any of the preceding embodiments, wherein the distance is determined with a resolution of at least 10 microns.

Embodiment 16: The system of any of the preceding embodiments, wherein the rangefinder is a time-domain optical coherence tomography system or a spectral domain optical coherence tomography system.

Embodiment 17: The system of any of the preceding embodiments, wherein the reference component is a last lens in the optical tracking system.

Embodiment 18: The system of any of the preceding embodiments, further comprising autofocusing the laser system in response to the distance.

Embodiment 19: The system of any of the preceding embodiments, the autofocusing comprising: measuring a distance to the stromal pigment of the iris at periodic intervals; and controlling, based on the distance, the laser system to remain substantially in focus between an anterior surface and posterior surface of the iris.

Embodiment 20: The system of any of the preceding embodiments, wherein the rangefinder comprises one or more of: triangulation lasers, time of flight detectors, phase shift detectors, ultrasonic detectors, frequency modulation detectors, interferometers, a camera, or a light sensor.

Embodiment 21: The system of any of the preceding embodiments, wherein the rangefinder is configured to be set to a coarse resolution for determining the distance for a coarse adjustment of the patient support structure or a fine resolution for determining the distance for a fine adjustment of the patient support structure.

Embodiment 22: The system of any of the preceding embodiments, wherein the coarse resolution is between 2000 microns and 6000 microns and the fine resolution is between 5 microns to 2000 microns.

Embodiment 23: The system of any of the preceding embodiments, wherein the coarse adjustment hardware is configured to be manually operated to perform a coarse adjustment based on the resolution set on the rangefinder and the system is configured to generate, during a coarse adjustment, an indication of the position of the anterior iris relative to a target position of the anterior iris.

Embodiment 24: The system of any of the preceding embodiments, wherein the coarse adjustment hardware is configured to be automatic to perform a coarse adjustment based on the resolution set on the rangefinder and the system is configured to generate, during a coarse adjustment, an indication of the position of the anterior iris relative to a target position of the anterior iris.

Embodiment 25: The system of any of the preceding embodiments, wherein the coarse adjustment hardware is configured to be automatic and the system is configured to automatically to perform a coarse adjustment based on the resolution set on the rangefinder.

Embodiment 26: The system of any of the preceding embodiments, the rangefinder configured to be set to a coarse resolution or a fine resolution and the distance being in an area of interest, wherein when the rangefinder is set to the coarse resolution the area of interest is larger than that when the rangefinder is set to the fine resolution.

Embodiment 27: The system of any of the preceding embodiments, wherein the coarse adjustment hardware is configured to be manually operated to perform a coarse adjustment based on the resolution set on the rangefinder and the system is configured to generate, during the coarse adjustment, an indication of the position of the anterior iris relative to a target position of the anterior iris.

Embodiment 28: The system of any of the preceding embodiments, wherein the coarse adjustment hardware is configured to be automatic to perform a coarse adjustment based on the resolution set on the rangefinder and the system is configured to generate, during a coarse adjustment, an indication of the position of the anterior iris relative to a target position of the anterior iris.

Embodiment 29: The system of any of the preceding embodiments, wherein the coarse adjustment hardware is configured to be automatic and the system is configured to automatically perform a coarse adjustment based on the resolution set on the rangefinder.

Embodiment 30: The system of any of the preceding embodiments, the rangefinder configured to be set to a coarse resolution or a fine resolution, the system configured to: perform a coarse adjustment of the patient support surface utilizing the coarse adjustment hardware; perform a fine adjustment of the patient support surface utilizing the fine adjustment hardware; and perform an ultra-fine adjustment of an element of the laser system.

Embodiment 31: The system of any of the preceding embodiments, wherein the element is a lens and performing the ultra-fine adjustment comprises adjusting a position of the lens to reduce a difference between a target distance and the distance as determined by the rangefinder.

Embodiment 32: The system of any of the preceding embodiments wherein the system is configured to perform the ultra-fine adjustment with a resolution of 5 microns or less.

Embodiment 33: The system of any of the preceding embodiments, wherein the laser system does not move such that only the patient support surface is configured to position the patient.

Embodiment 34: The system of any of the preceding embodiments, wherein the laser system is cantilevered over the patient support surface.

Embodiment 35: The system of any of the preceding embodiments, further comprising: a physician console in communication with the laser system and physically detached from the laser system, wherein the physician console is configured to display patient data including one or more of patient images, patient medical record data, or patient treatment data associated with the color alteration procedure performed by the laser system.

Embodiment 36: The system of any of the preceding embodiments, the physician console further configured to accept input at the physician console that controls the laser system and/or the patient support structure.

Embodiment 37: The system of any of the preceding embodiments, further comprising a technician console in communication with the laser system and physically detached from the laser system and the physician console.

Embodiment 38: The system of any of the preceding embodiments, wherein the physician console and the technician console are configured to be in communication to view real-time images and the patient treatment data associated with the color alteration procedure.

Embodiment 39: The system of any of the preceding embodiments, wherein the physician console is configured to override commands for the laser system that were initiated by the technician console.

Embodiment 40: The system of any of the preceding embodiments, further comprising an image sensor and a non-transitory, machine-readable medium storing instructions which, when executed by at least one programmable processor, cause the at least one programmable processor to perform operations comprising: capturing a first scan with an image sensor and at a first time prior to the altering of the eye color, the first scan being of at least one of an iris or retina of the patient; capturing a second scan with the image sensor and at a second time later than the first time and prior to the altering of the eye color, the second scan being of at least one of the iris or the retina of the patient; comparing the first scan captured at the first time with the second scan captured at the second time; determining an identity of the patient based on matching the first scan captured at the first time with the second scan captured at the second time; generating for display, on a user interface, a confirmation of the identity of the patient; retrieving patient medical record data based on the first scan or the second scan; and displaying, at a physician console, the patient medical record data based on the iris scan.

Embodiment 41: The system of any of the preceding embodiments, the operations further comprising: retrieving a treatment plan for delivery by the laser system; and enabling the laser system to deliver the treatment plan based on the first scan or the second scan corresponding to patient identification included with the patient medical record data.

A tangible, non-transitory, machine-readable medium storing instructions that, when executed by a data processing apparatus, cause the data processing apparatus to perform operations comprising those described in any of the above system embodiments 1-41.

A method comprising operations described in any of the above system embodiments 1-41.

What is claimed is:

1. A system for supporting and aligning a patient during a color alteration procedure of a patient's eye, the system comprising:
    a laser system for performing the color alteration procedure, wherein the laser system delivers a laser light in a first direction to perform the color alteration procedure;
    a control computer system adjacent to the laser system for controlling the laser system during the color alteration procedure, the control computer system comprising a user interface in a first plane substantially perpendicular to the first direction; and
    a patient support structure comprising:
        a patient support surface extending in a second direction that is substantially perpendicular to the first direction and configured to be adjustable to set a patient position or alignment relative to the laser system;
        coarse adjustment hardware configured to cause automated and/or manual adjustments to the patient support surface in the first direction; and
        fine adjustment hardware configured to cause automated fine adjustments to the patient support surface in the first direction based on instructions received from the control computer; and
    a non-transitory, machine-readable medium storing instructions which, when executed by the control computer system, cause the control computer system to perform operations comprising automatically performing fine adjustments utilizing the fine adjustment hardware based on a treatment plan for altering an eye color of the patient.

2. The system of claim 1, further comprising an image sensor and wherein the operations further comprise:
    capturing a first scan with an image sensor and at a first time prior to the altering of the eye color, the first scan being of at least one of an iris or retina of the patient;
    capturing a second scan with the image sensor and at a second time later than the first time and prior to the altering of the eye color, the second scan being of at least one of the iris or the retina of the patient;
    comparing the first scan captured at the first time with the second scan captured at the second time;
    determining an identity of the patient based on matching the first scan captured at the first time with the second scan captured at the second time;
    generating for display, on a user interface, a confirmation of the identity of the patient;
    retrieving patient medical record data based on the first scan or the second scan; and
    displaying, at a physician console, the patient medical record data based on the iris scan.

3. The system of claim 2, the operations further comprising:
    retrieving a treatment plan for delivery by the laser system; and
    enabling the laser system to deliver the treatment plan based on the first scan or the second scan corresponding to patient identification included with the patient medical record data.

4. The system of claim 1, the patient support structure comprising a head support element configured to cause a head of the patient to be supported without engagement of neck muscles.

5. The system of claim 4, the patient support structure comprising a lower support portion and an upper reclining portion, the head support element mounted to the upper reclining portion and the head support element is adjustable to set the patient position or alignment.

6. The system of claim 1, wherein the coarse adjustment hardware is further configured to move the patient support surface substantially perpendicular to the first direction or the coarse adjustment hardware being a manual adjustment system that is configured to adjust the patient position to be in a direction substantially parallel to an optical axis of the laser system.

7. The system of claim 1, the fine adjustment hardware comprising a hydraulic system configured to cause adjustment of the patient support surface with a resolution of 10 millimeters or less.

8. The system of claim 1, further comprising an optical tracking system that includes a rangefinder utilized to determine a distance between the iris and a reference component of the optical tracking system.

9. The system of claim 8, wherein the distance is determined with a resolution of at least 750 microns.

10. The system of claim 8, further comprising autofocusing the laser system in response to the distance.

11. The system of claim 10, the autofocusing comprising:
measuring a distance to the stromal pigment of the iris at periodic intervals; and
controlling, based on the distance, the laser system to remain substantially in focus between an anterior surface and posterior surface of the iris.

12. The system of claim 8, the rangefinder configured to be set to a coarse resolution or a fine resolution and the distance being in an area of interest, wherein when the rangefinder is set to the coarse resolution the area of interest is larger than that when the rangefinder is set to the fine resolution.

13. The system of claim 8, wherein the rangefinder is configured to be set to a coarse resolution for determining the distance for a coarse adjustment of the patient support structure or a fine resolution for determining the distance for a fine adjustment of the patient support structure.

14. The system of claim 13, wherein the coarse resolution is between 2000 microns and 6000 microns and the fine resolution is between 5 microns to 2000 microns.

15. The system of claim 13, wherein the coarse adjustment hardware is configured to be manually operated to perform a coarse adjustment based on the resolution set on the rangefinder and the system is configured to generate, during the coarse adjustment, an indication of the position of the anterior iris relative to a target position of the anterior iris.

16. The system of claim 13, wherein the coarse adjustment hardware is configured to be automatic to perform a coarse adjustment based on the resolution set on the rangefinder and the system is configured to generate, during the coarse adjustment, an indication of the position of the anterior iris relative to a target position of the anterior iris.

17. The system of claim 13, wherein the coarse adjustment hardware is configured to be automatic and the system is configured to automatically perform a coarse adjustment based on the resolution set on the rangefinder.

18. The system of claim 13, wherein the coarse adjustment hardware is configured to be manually operated to perform a coarse adjustment based on the resolution set on the rangefinder and the system is configured to generate, during the coarse adjustment, an indication of the position of the anterior iris relative to a target position of the anterior iris.

19. The system of claim 13, wherein the coarse adjustment hardware is configured to be automatic to perform a coarse adjustment based on the resolution set on the rangefinder and the system is configured to generate, during a coarse adjustment, an indication of the position of the anterior iris relative to a target position of the anterior iris.

20. The system of claim 13, wherein the coarse adjustment hardware is configured to be automatic and the system is configured to automatically perform a coarse adjustment based on the resolution set on the rangefinder.

21. The system of claim 8, the rangefinder configured to be set to a coarse resolution or a fine resolution, the system configured to:
perform a coarse adjustment of the patient support surface utilizing the coarse adjustment hardware;
perform a fine adjustment of the patient support surface utilizing the fine adjustment hardware; and
perform an ultra-fine adjustment of an element of the laser system.

22. The system of claim 21, wherein the system is configured to perform the ultra-fine adjustment with a resolution of 5 microns or less.

23. The system of claim 1, further comprising:
a physician console in communication with the laser system and physically detached from the laser system, wherein the physician console is configured to display patient data including one or more of patient images, patient medical record data, or patient treatment data associated with the color alteration procedure performed by the laser system.

24. The system of claim 23, the physician console further configured to accept input at the physician console that controls the laser system and/or the patient support structure.

25. The system of claim 23, further comprising a technician console in communication with the laser system and physically detached from the laser system and the physician console.

26. The system of claim 25, wherein the physician console and the technician console are configured to be in communication to view real-time images and the patient treatment data associated with the color alteration procedure.

27. The system of claim 26, wherein the physician console is configured to override commands for the laser system that were initiated by the technician console.

* * * * *